(12) United States Patent
Cheney

(10) Patent No.: US 10,117,647 B2
(45) Date of Patent: Nov. 6, 2018

(54) ELASTIC ORTHOPEDIC IMPLANT AND METHOD OF MANUFACTURING THEREOF

(71) Applicant: BioMedical Enterprises, Inc., San Antonio, TX (US)

(72) Inventor: Daniel F. Cheney, San Antonio, TX (US)

(73) Assignee: BioMedical Enterprises, Inc, San Antonio, TX (US)

( * ) Notice: Subject to any disclaimer, the term of this patent is extended or adjusted under 35 U.S.C. 154(b) by 260 days.

(21) Appl. No.: 15/254,578

(22) Filed: Sep. 1, 2016

(65) Prior Publication Data

US 2017/0065275 A1   Mar. 9, 2017

Related U.S. Application Data

(60) Provisional application No. 62/213,774, filed on Sep. 3, 2015.

(51) Int. Cl.
*A61B 17/064* (2006.01)
*A61B 17/00* (2006.01)

(52) U.S. Cl.
CPC ........ *A61B 17/064* (2013.01); *A61B 17/0642* (2013.01); *A61B 2017/00526* (2013.01); *A61B 2017/00867* (2013.01); *A61B 2017/0641* (2013.01); *A61B 2017/0645* (2013.01)

(58) Field of Classification Search
CPC ........ A61B 17/0642; A61B 2017/0641; A61B 17/064
See application file for complete search history.

(56) References Cited

U.S. PATENT DOCUMENTS

| | | | |
|---|---|---|---|
| 1,106,241 A | | 8/1914 | Richardson |
| 2,544,492 A | * | 3/1951 | Downing ............... A61B 17/10 |
| | | | 227/181.1 |
| 3,939,828 A | | 2/1976 | Mohr et al. |

(Continued)

FOREIGN PATENT DOCUMENTS

| EP | 0127994 A1 | 12/1984 |
|---|---|---|
| EP | 0682920 A1 | 2/1995 |

(Continued)

OTHER PUBLICATIONS

4-Fusion Shape Memory Implant Training Slide Images, Memometal, Inc., 2008.

(Continued)

*Primary Examiner* — Christian Sevilla
(74) *Attorney, Agent, or Firm* — Christopher L. Makay

(57) ABSTRACT

An orthopedic implant includes a bridge and at least a first leg extending from a first end of the bridge and a second lee extending from the second end of the bridge. The bridge includes a first upper section and a second lower section. The first upper section includes surfaces that are non-orthogonal and taper from a central surface to provide the first upper section with a non-uniform cross-section. The second lower section includes surfaces that are non-orthogonal and taper from a central surface to provide the second lower section with a non-uniform cross-section. The non-uniform cross-sections of the first upper section and the second lower section flatten the profile of the bridge, thereby producing an orthopedic implant with a smooth composite surface.

28 Claims, 25 Drawing Sheets

(56) References Cited

U.S. PATENT DOCUMENTS

| | | | | |
|---|---|---|---|---|
| 4,269,180 | A * | 5/1981 | Dall | A61B 17/0642 606/281 |
| 4,438,769 | A * | 3/1984 | Pratt | A61B 17/0642 227/147 |
| 4,592,346 | A * | 6/1986 | Jurgutis | A61B 17/0642 411/457 |
| 4,665,906 | A | 5/1987 | Jervis | |
| 4,869,243 | A | 9/1989 | Huene | |
| 5,067,957 | A | 11/1991 | Jervis | |
| 5,171,252 | A | 12/1992 | Friedland | |
| 5,246,443 | A | 9/1993 | Mai | |
| 5,779,707 | A | 7/1998 | Bertholet et al. | |
| 5,785,713 | A | 7/1998 | Jobe | |
| 6,001,110 | A | 12/1999 | Adams | |
| 6,187,009 | B1 | 2/2001 | Herzog et al. | |
| 6,268,589 | B1 | 7/2001 | Flot | |
| 6,323,461 | B2 | 11/2001 | Flot | |
| 6,412,639 | B1 | 7/2002 | Hickey | |
| 6,607,542 | B1 | 8/2003 | Wild | |
| 6,685,708 | B2 | 2/2004 | Monassevitch et al. | |
| 6,783,531 | B2 | 8/2004 | Allen | |
| 7,240,677 | B2 | 7/2007 | Fox | |
| 7,344,539 | B2 | 3/2008 | Serhan et al. | |
| 7,556,647 | B2 | 7/2009 | Drews et al. | |
| 7,867,265 | B2 | 1/2011 | Beutter | |
| 8,118,952 | B2 | 2/2012 | Gall et al. | |
| 8,137,351 | B2 | 3/2012 | Prandi | |
| 8,191,220 | B2 | 6/2012 | Magnuson et al. | |
| 8,211,109 | B2 | 7/2012 | Groiso | |
| 8,584,853 | B2 | 11/2013 | Knight et al. | |
| 8,596,514 | B2 | 12/2013 | Miller et al. | |
| 2005/0043757 | A1 | 2/2005 | Arad et al. | |
| 2005/0009660 | A1 | 5/2005 | Allen | |
| 2005/0107807 | A1 | 5/2005 | Nakao | |
| 2009/0062800 | A1 | 3/2009 | Shano | |
| 2009/0272786 | A1 | 11/2009 | Zeiner et al. | |
| 2010/0133316 | A1 | 6/2010 | Lizee et al. | |
| 2012/0024937 | A1 | 2/2012 | Allen | |
| 2012/0209305 | A1 | 8/2012 | Deodhar et al. | |
| 2013/0026206 | A1 | 1/2013 | Fox | |
| 2013/0026207 | A1 | 1/2013 | Fox | |
| 2013/0030437 | A1 | 1/2013 | Fox | |
| 2013/0030438 | A1 | 1/2013 | Fox | |
| 2013/0184768 | A1 | 7/2013 | McIff et al. | |
| 2013/0231667 | A1 | 9/2013 | Taylor et al. | |
| 2014/0018809 | A1 | 1/2014 | Allen | |
| 2014/0097228 | A1 | 4/2014 | Taylor et al. | |
| 2014/0276830 | A1 | 9/2014 | Cheney | |
| 2014/0277516 | A1 | 9/2014 | Miller et al. | |
| 2015/0257801 | A1 | 9/2015 | Palmer et al. | |
| 2016/0015384 | A1 | 1/2016 | Roedl et al. | |

FOREIGN PATENT DOCUMENTS

| | | | |
|---|---|---|---|
| EP | 0857462 | A1 | 1/1998 |
| EP | 0826340 | A2 | 3/1998 |
| EP | 1870042 | A1 | 12/2007 |
| WO | 2008129061 | A1 | 10/2008 |
| WO | 2013055824 | A1 | 4/2013 |

OTHER PUBLICATIONS

4-Fusion Shape Memory Implant Brochure, Memometal, Inc., Jun. 23, 2009.

MemoGraph Brochure, M.B.A. (Memory Biological Application), Parc Club de Nancy de Brabois, Batiment B11, 4 allee Vincennes, 54500 Vandceurve, France, 1999.

OSStaple Brochure Including pictures of staple loaded in shipping block, BioMedical Enterprises, Inc., 14875 Omicron Drive, Suite 205, San Antonio, TX 78245, 2010.

E. A. Van Amerongen et al., "Four-Corner Arthrodesis Using the Quad Memory Staple," Journal of Hand Surgery (European vol. 2008) (Jan. 7, 2009).

U. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.

T. F. Smith, "The Bone Staple: Tried and True Superhero of Bone Fixation," Educational Materials Update Chapter 41 (2010) available at www.podiatryinstitute.com/pdfs/Update 2010/2010 41.pdf.

ELEVEST Procedure Kit, Instructions for Use by CooperSurgical (© 2007).

Agee WristJack, Surgeon's Manual by Hand BioMechanics Labs, Inc. (© 1990-2002).

Development of a Nickel-Titanium Shape Memory Alloy Bone Repair Staple and Other in-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).

Superelastic Fixation System Brochure, Memometal Inc., USA, Aug. 12, 2009.

Shape Memory Staple System for Arthrodesis and Skeletal Fixation of the Hand Brochure, Core Essence Orhtopaedics, Inc., 2009.

ENTact™ Septal Stapler, Product brochure by ENTrigue Surgical, Inc. (© 2009).

R. M. Sloan et al., "Orthopedic Fixation Devices," Radiographics at 823 (Sep. 1991).

J. Arthur, "Improving Operating Efficiency in Five Days," Lean Six Sigma for Hospitals, McGraw-Hill (2011).

K. Yamauchi et al. (ed.), "Shape Memory and Superelastic Alloys: Applications and Technologies" (2011).

BioResearch Innovations (BRI), "Memodyn Compression Staple," FDA 510(K) disclosure (Jan. 2004).

G. C. Taylor et al., "Complications of Internal Fixation," Podiatry Institute Educational Materials Update Chapter 79 (1992).

Wright Medical Technology, Inc., "Charlotte Compression Staple as described by Robert Anderson, MD; Bruce Cohen, MD; and W. Hodges Davis, MD" (2007).

A. A. Weinbroum et al., "Efficiency of the Operating Room Suite," American Journal of Surgery 244-250 (2003).

G. G. Porto, "Safety by Design: Ten Lessons From Human Factors Research," Journal of Healthcare Risk Management 43-50 (Fall 2011).

Scott M. Russell, Design Considerations for Nitinol Bone Staples, Journal of Materials Engineering and Performance, vol. 18(5-6), Aug. 2009, USA.

* cited by examiner

ELASTIC ORTHOPEDIC IMPLANT AND METHOD OF MANUFACTURING THEREOF

BACKGROUND OF THE INVENTION

1. Field of the Invention

The present invention relates generally to a method of use and manufacture of an orthopedic implant, and, more particularly, but not by way of limitation, to an orthopedic implant that features a lower profile, beveled edges, and more strength than conventional orthopedic implants.

2. Description of the Related Art

Common orthopedic implants for use in fixating bones together include orthopedic staples. Conventional orthopedic staples have a bridge that connects two or more legs. To fixate bones during surgery, the surgeon drills holes in two bones, or two bone fragments, and then inserts the legs of the orthopedic staple into the holes. The legs can be smooth or have barbs to resist pull out from the bone. Orthopedic implants for use in fixating bones together include several types. Conventional rigid orthopedic staples have a bridge connecting two or more legs and do not create any lasting compression of the two bones. Improvements on conventional rigid orthopedic staples are orthopedic staples made from a shape memory material such as nitinol.

Orthopedic staples made from a shape memory material include a bridge connecting two or more legs wherein the legs converge towards one another at the tips. The advantage of shape memory orthopedic staples is that they can create lasting compression between bones or bone fragments. Specifically, shape memory orthopedic staples can be temporarily distorted within their elastic strain limits so that the legs are parallel. Having the legs parallel allows the staple implant to be inserted into two bones or bone fragments. After insertion and upon release, and, if necessary upon heating to the proper temperature, the implant will return to its converging shape and thus squeeze the two bones or bone fragments together thereby creating lasting compression.

FIGS. 1-6 illustrate a prior art shape memory implant 10. The bridge 3 of the implant 10 has four surfaces, a top surface 20, two side surfaces 21 and 22, and a bottom surface 23. The top surface 20 has a surface normal that points upwards, the bottom surface 23 has a surface normal that points downwards, and the side surfaces 21 and 22 have surface normals that are directed orthogonal to the surface normal of top surface 20. FIGS. 1 and 2 illustrate the implant 10 in an insertion position 100 with legs 1 and 2 parallel to each other and perpendicular to a bridge 3. As illustrated in FIG. 2, angle alpha is approximately 90 degree in the insertion position 100. Furthermore, in the insertion position, the bridge 3 is a uniform height from corner 4 to corner 5.

FIG. 3 illustrates the implant 10 in an implanted position 150 wherein leg tips 6 and 7 of the legs 1 and 2 are closer together than the insertion position 100. Specifically, the corners 4 and 5 produce rotational torque to squeeze the tips 6 and 7 together thereby creating a compressive force between the legs 1 and 2. Furthermore, in the implanted position, the bridge 3 of implant 10 is slightly arched helping to create a compressive force between legs 1 and 2.

Whether the implant 10 is in the insertion position 100 or the implanted position 150, the bridge 3 of the implant 10 has a uniform thickness from end to end. FIGS. 4 and 5 illustrate a top view and a side view of the implant 10 showing the bridge 3 has an approximate rectangular cross-section. In particular, the cross-section of the bridge 3 is uniform from a corner 4 to a corner 5 and across the length of the bridge 3. The uniform thickness from end to end of the bridge 3 creates sharp edges that may be felt as a rectangular lump by the patient after surgery.

FIG. 6 illustrates the implant 10 implanted into a bone 200. The implant 10 is placed into the insertion position 100 and inserts into the bone 200. The implant 10 then moves from the insertion position 100 to the implanted position 150 due to stored energy in the shape memory implant 10. After the implant 10 is implanted into the bone 200 the top surface 20 of the bridge and the side surfaces 21 and 22 form a rectangular lump that would be present on top of the bone 200 and under the soft tissue of a patient.

FIGS. 7-9 illustrate a prior art shape memory implant 50 disclosed in U.S. Pat. No. D705,930S. The implant 50 includes legs 56 and 57 connected with abridge 51. The bridge 51 of the implant 50 has four surfaces, atop surface 52, two side surfaces 53 and 54, and a bottom surface 55. The top surface 52 has a surface normal that points upwards, and the bottom surface 55 has a surface normal that points downwards. The top surface 52 is wider than the bottom surface 55 such that the side surfaces 53 and 54 taper from the top surface 52 towards the bottom surface 55. As a result, the bridge 51 is wider than the legs 56 and 57, which increases the strength of the implant 50.

FIGS. 7-9 illustrate the implant 50 in an implanted position wherein leg tips 59 and 60 of the legs 56 and 57 are closer together than in an insertion position where the legs 56 and 57 are parallel to each other and perpendicular to abridge 51. Specifically, in the implanted position, the corners 61 and 62 produce rotational torque to squeeze the tips 59 and 60 together thereby creating a compressive force between the legs 56 and 57. Furthermore, in the implanted position, the bridge 51 of implant 50 is slightly arched helping to create a compressive force between legs 56 and 57.

Whether the implant 50 is in the insertion position or the i ted position, the bridge 51 of the implant 50) has a uniform thickness from end to end. In particular, the cross-section of the bridge 51 is uniform from the corner 61 to the corner 62 and across the length of the bridge 51. The uniform thickness from end to end of the bridge 51 creates edges that may be felt as a lump by the patient after surgery.

FIG. 10 illustrates a prior art implant 610 in an insertion position 750. The implant 610 includes a bridge 605 and four legs 601-604. The bridge 605 spans and connects the four legs 601-604 at corners 606-609. The bridge 605 of the implant 610 has a uniform height between the four legs 601-604, and the top surface has a normal that is directed vertically upwards. The bridge 605 of the implant 610 has across-sectional profile that is substantially similar to the bridge 3 of the implant 10 in that the bridge 605 of the implant 610 has a uniform thickness from end to end. As such, the implant 610 like the implant 10 creates sharp edges that may be felt as a rectangular lump by the patient after surgery.

In addition to the prior art staple described above, there are other shape memory orthopedic staples on the market today. The Stryker Easy Clip™ implant is a nitinol implant with abridge connecting two converging legs. It is mechanically distorted so that the legs are in a parallel shape via a metal instrument. The same metal instrument is used to insert the legs into bone, and then releases the staple. U.S. Pat. No. 8,584,853 B2 and related U.S. Pat. No. D 705,930S, U.S. Pat. No. D691,720S, and U.S. Pat. No. D706,927S, as previously described with respect to FIGS. 7-9, are nitinol implants with a bridge that connects two or more converging legs. These implants are pre-loaded onto insertion tools that maintain the leas in parallel position for later insertion into bone. The Stryker Easy Clip™ and the products disclosed in U.S. Pat. No. 8,584,853 B2; U.S. Pat. No. D 705,930S; U.S. Pat. No. D691,720S; and U.S. Pat. No. D706,927S are examples of nitinol implants wherein the bridge has a uniform width and thickness across the entire implant. Specifically, a cross section taken orthogonal to the bridge at any location between the legs would show the same cross-section height.

There are various methods of manufacturing elastic shape memory implants such as the Stryker Easy Clip™ as well as the implants 10, 50, and 610. The Stryker Easy Clip™ can be manufactured by electrical discharge machining from a flat plate. The implants 10 and 50 can be manufactured by electrical discharge machining or a similar method from a billet. The implant 610 can be manufactured from a flat sheet of material. Specifically, the implant 610 is cut from a flat sheet and the legs 601-604 are then bent into the final shape. Regardless, of whether implants are manufactured using electrical discharge machining, or manufactured from a flat plate or billet of material, the implants 10, 50, and 610 feature a uniform bridge thickness such that the patient would feel the full thickness of bridge at all locations.

As described above, the existing prior art orthopedic implants have bridges with uniform thickness from end to end after they are manufactured. In particular, a cross section taken orthogonal to the bridge at any location between the legs would show the same cross-section height. This design can potentially create a bulge or protuberance after surgery that can be fell by a patient as a lump under their skin. After manufacture, and to mitigate the problems associated with having a bridge with uniform thickness, the edges of the prior a implants may he rounded by mechanical tumbling or acid etching. However, even after mechanical tumbling or acid etching the surfaces that make up the bridge are orthogonal to each other and the bridge still has a uniform thickness that can potentially be felt by a patient. Furthermore, mechanical tumbling or acid etching an implant after manufacture increases costs.

Accordingly, a shape memory implant design and a method of manufacture thereof that has a lower profile and tapered shape at the time of manufacturing, does not have orthogonal bridge surfaces, has greater strength than prior art implants, and creates less of a bulge or protuberance under the skin would be beneficial.

SUMMARY OF THE INVENTION

In accordance with the present invention, an elastic orthopedic staple implant includes a bridge that connects two or more lees. The implant has a natural shape with the two or more legs converging towards each other. Each of the legs can either be smooth, or have barbs to increase pull-out resistance from bone. The legs can either be homgeneous with the bridge, such that it is made from the same material, or the legs could be screws and made from a different material.

The bridge design of the implant has slanted surfaces that result in tapered upper and lower surfaces. These surfaces are not orthogonal to each other, which, therefore, results in a more smoothed composite surface. The tapered upper surface of the bridge results in a cross-sectional thickness that is lower than a conventional implant, and less of a protuberance to a patient. Similarly, the lower surface of the bridge is tapered to allow the implant to lie more flat. The bridge design of the implant is also such that the bridge is wider than the legs. This allows for the bridge to have greater bending strength than a comparable prior art implant, because most prior art implants have a bridge width that matches the width of the leg.

The implant can be elastically deformed to a temporary insertion shape with legs that are parallel to each other. One way of elastically deforming the implant is done by deforming the legs relative to the bridge, which in effect increases an acute angle between the leg and bridge to become a right angle. By stretching the converging legs simultaneously, all of the acute angles become right angles and are thus parallel. Alternatively, the implant can be deformed by stretching the bridge. In this case, the angles between legs and bridge are all right angles, and the stretching of the bridge rotates all legs from converging to parallel position simultaneously.

The elastic implant of this invention can be made from a solid billet of material. The material can be cut from two orthogonal directions, using a single continuous cutting motion from each of the two directions. When finished, the implant with advanced bridge design and superior strength can be retrieved from the solid billet. The cutting motion for each orthogonal surface is a continuous path with uniform thickness.

DETAILED DESCRIPTION OF THE PREFERRED EMBODIMENTS

Figure 1:
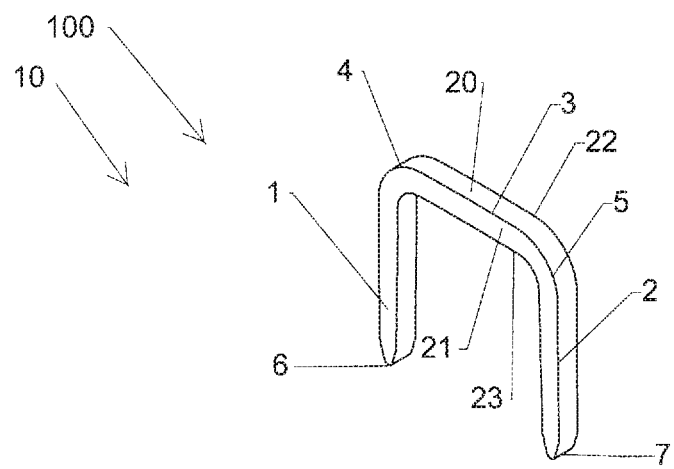
FIG. 1 is a perspective view illustrating a shape memory implant according to the prior art.
Figure 2:
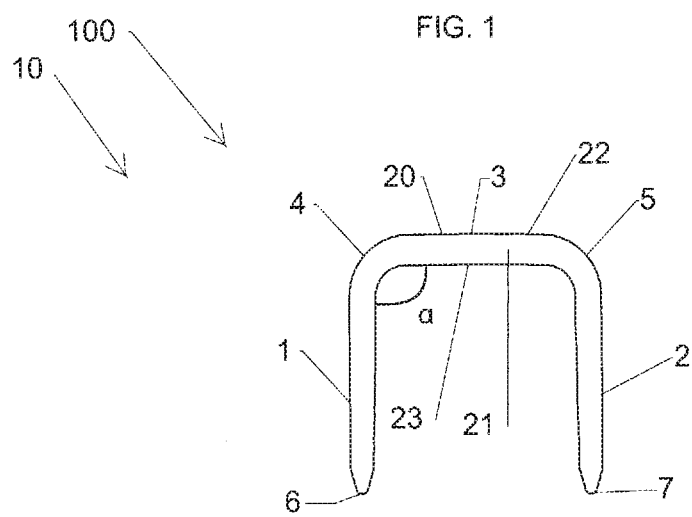
FIG. 2 is a side view illustrating the shape memory implant according to the prior art with its legs parallel.
Figure 3:
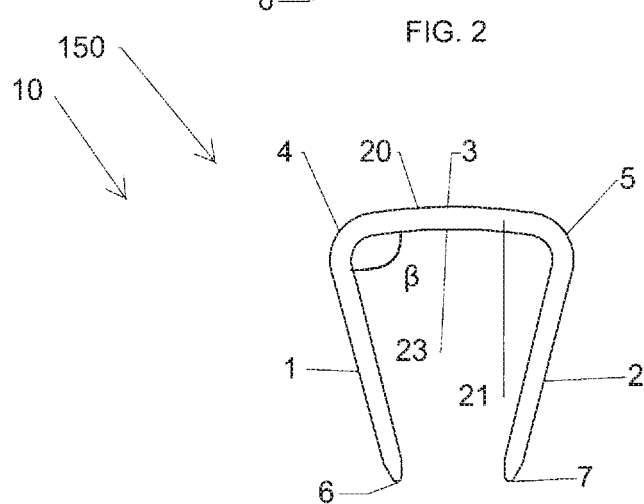
FIG. 3 is a side view illustrating the shape memory implant according to the prior art with its legs converging.
Figure 4:
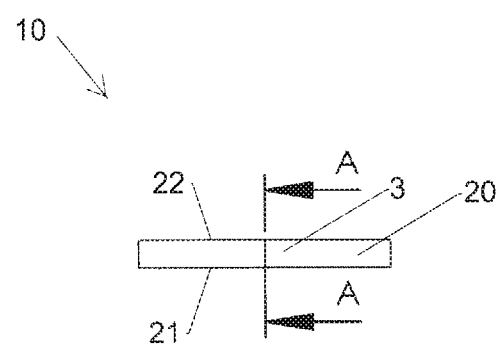
FIG. 4 is a top view illustrating the shape memory implant according to the prior art.
Figure 5:
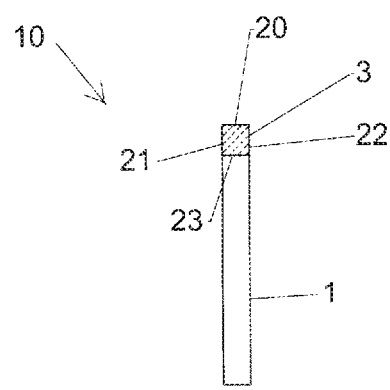
FIG. 5 is cross-sectional side view taken along lines A-A in FIG. 4 illustrating the shape memory implant according to the prior art.
Figure 6:
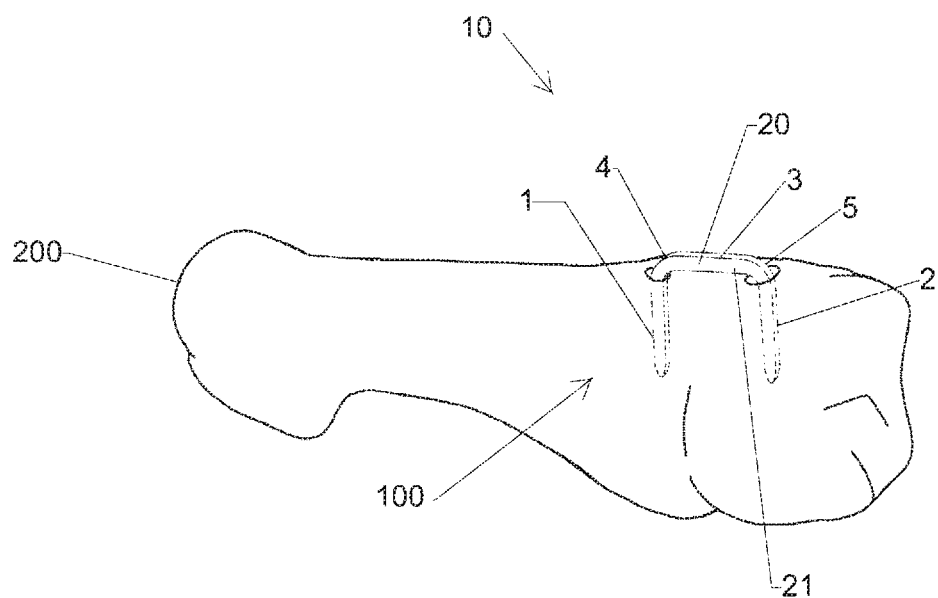
FIG. 6 is a perspective view illustrating shape memory implant according to the prior art after implantation into a bone.
Figure 7:
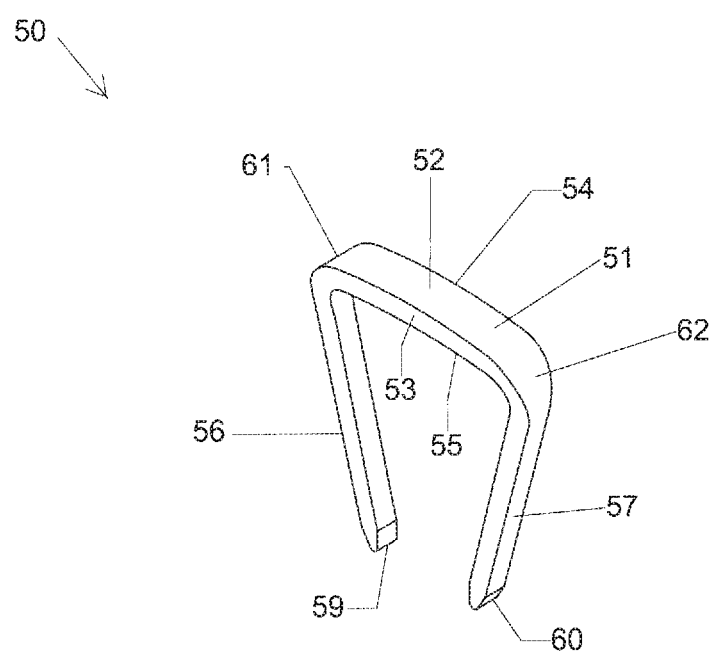
FIG. 7 is a perspective view illustrating a shape memory implant according to the prior art.
Figure 8:
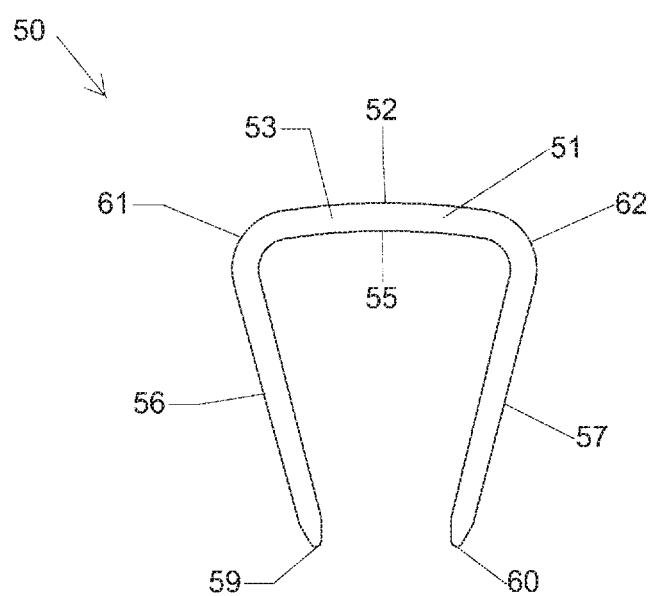
FIG. 8 is a front view illustrating the shape memory implant according to the prior art.
Figure 9:
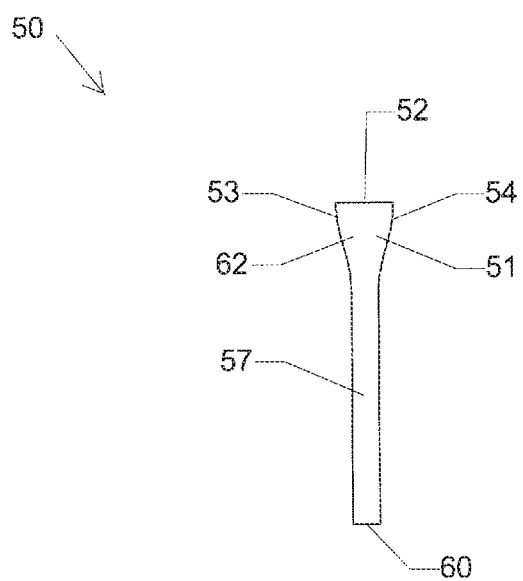
FIG. 9 is a side view illustrating the shape memory implant according to the prior art.
Figure 10:
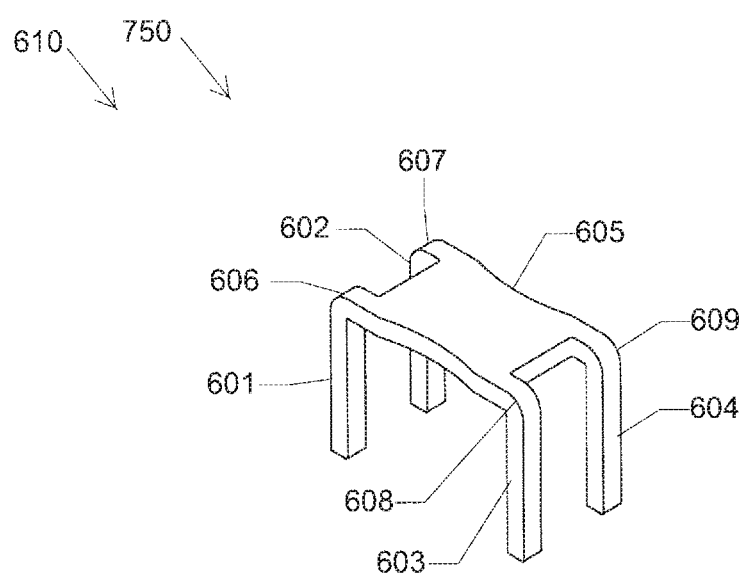
FIG. 10 is a perspective view illustrating a shape memory implant according to the prior art.
Figure 11:
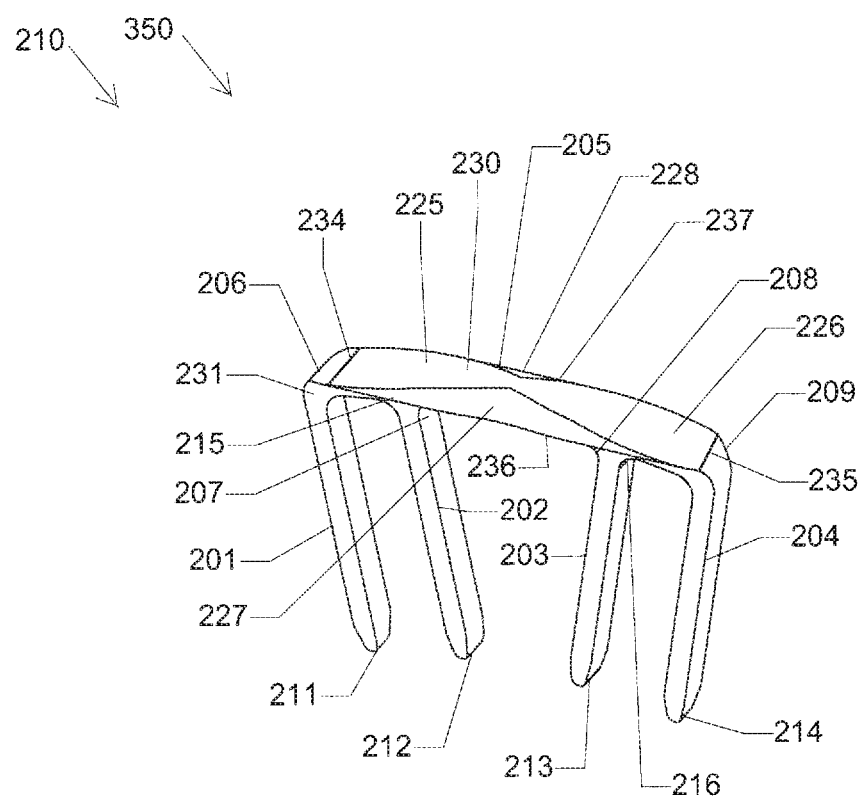
FIGS. 11 and 12 are a perspective views illustrating an implant according to a first embodiment with its legs converging.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 11-27 illustrate a first embodiment of an elastic implant 210. The implant 210 is shown in a converging position 350. The implant 210 can be made from any elastic material. An example of such a material is a shape memory implant made from nitinol. The implant 210 includes a bridge 205 and four legs 201-204. The bridge 205 connects with the legs 201-204. Each leg 201-204 has a tip 211-214, respectively, shown converging towards the middle of the implant 210. The legs 201-204 are smooth; however, it is possible to include barbs on legs 201-204 to improve the pull-out resistance of the implant 210. The implant 210 includes corners 206-209 and 215-216. In the first embodiment, the corners 206-209 store energy when deformed and create a compressive force that moves tips 211-214 towards the center of the implant 210.

The bridge 205 includes a first upper section 230 and a second lower section 231. The first upper section 230 is the portion of the bridge 205 that lies above a plane 232 and the second lower section 231 is the portion of the bridge 205 that lies below the plane 232. The first upper section 230 includes a central surface 233 and first, second, third, and fourth surfaces 225-228. The central surface 233 may be linear to lower the profile of the first upper section 230. Alternatively, the central surface 233 may be non-linear to provide a smooth transition from the central surface 233 to each of the first, second, third, and fourth surfaces 225-228. The first surface 725 is non-linear and tapers from the central surface 233 to a first end transition 234 between the first upper section 230 and the second lower section 231. The second surface 226 is non-linear and tapers from the central surface 233 to a second end transition 235 between the first upper section 230 and the second lower section 231. The third surface 227 is non-linear and tapers from the central surface 233 to a first side transition 236 between the first upper section 230 and the second lower section 231. The fourth surface 228 is non-linear and tapers from the central surface 233 to a second side transition 237 between the first upper section 230 and the second lower section 231. In the first embodiment, the first, second, third, and fourth surfaces 225-228 each taper from the central surface 233 at an angle of between 5 degrees and 85 degrees when measured from a plane tangent to the central surface 233. The tapering of the first, second, third, and fourth surfaces 225-228 from the central surface 233 provides the implant 210 with a first upper section 230 that has a smooth composite surface and a non-uniform cross-sectional thickness between the first and second end transitions 234 and 235 as illustrated in FIGS. 21-23 and 25-27. As a result, the implant 210 includes a low profile and provides less of protuberance to a patient.

The second lower section 231 includes a central surface 240 and first and second surfaces 241 and 242. The central surface 240 is non-linear to provide a smooth transition from the central surface 240 to each of the first and second surfaces 241 and 242. The first surface 241 is non-linear and tapers from the central surface 240 to a first leg transition 243 between the second lower section 231 and the leg 201. The second surface 242 is non-linear and tapers from the central surface 240 to a second leg transition 244 between the second lower section 231 and the leg 204. The central surface 240 and first and second surfaces 241 and 242 may follow a substantially same non-linear path between the first and second leg transitions 243 and 244. Alternatively, the curvature of the non-linear path for the central surface 240 may be greater than the curvature of the non-linear paths for the first and second surfaces 241 and 242 in order to lessen the cross-sectional area of the second lower section 231 at the central surface 240. The non-linear paths followed by each of the central surface 240 and the first and second surfaces 241 and 242 provides the implant 210 with a second lower section 231 that flattens the profile of the implant 210, resulting in less protuberance to a patient. In the first embodiment, the second low section 231 is wider than the legs 201-204 in order to provide the implant 210 with increased bonding strength.

Figure 12:
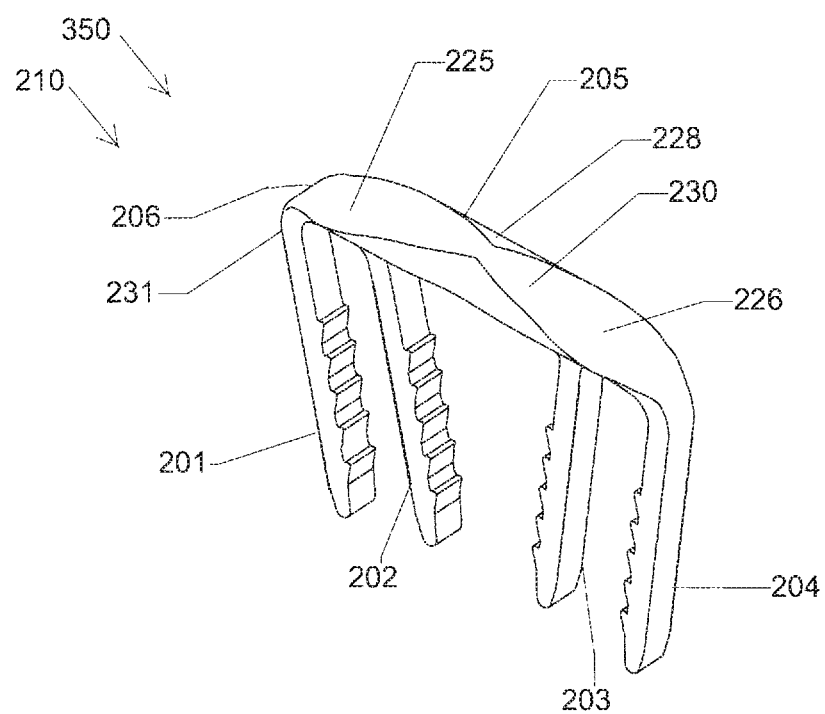
Figure 13:
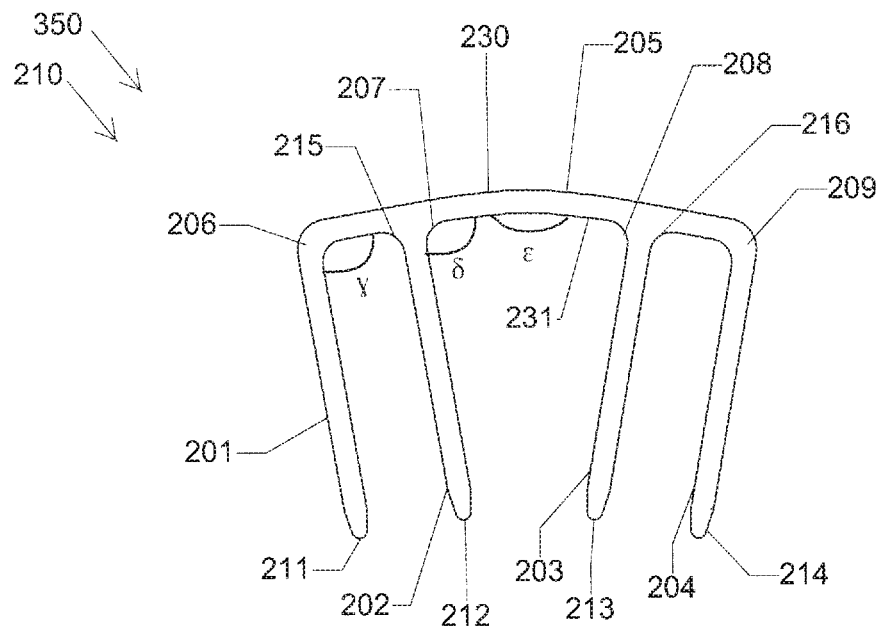
FIG. 13 is a side view illustrating the implant according to the first embodiment with its legs converging.
Figure 14:
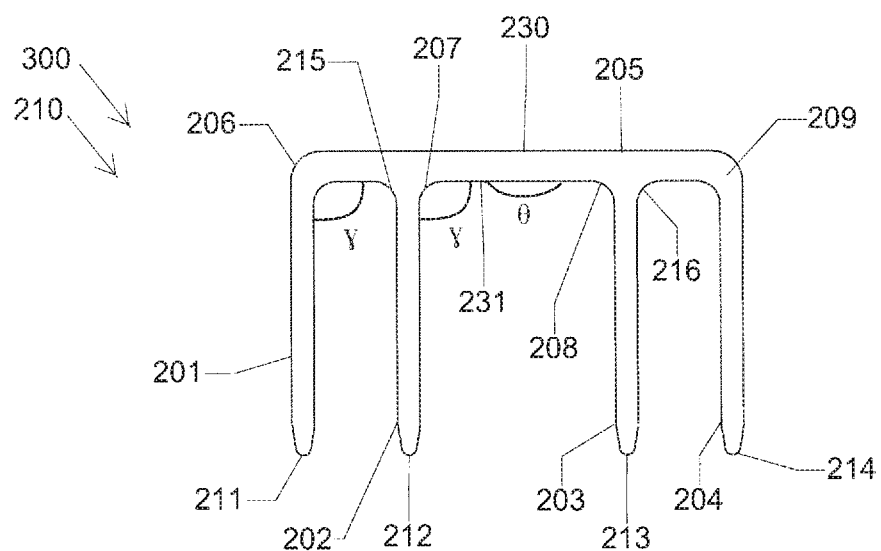
FIG. 14 is a side view illustrating the implant according to the first embodiment with its legs parallel.

FIG. 12 illustrates the implant 210 in the converging position 350 and with barbs on legs 201-204. FIG. 13 is a side view illustrating the implant 210 in the converging position 350, with legs 201-204 converging to the center, while FIG. 14 is a side view illustrating the implant 210 in an insertion position 300, with legs 201-204 substantially parallel. As illustrated in FIG. 13, the bridge 205 has been manufactured such that there are tapers on bridge 205 towards the edges of the bridge, labeled as first, second, third, and fourth surfaces 225-228. The first, second, third, and fourth surfaces 225-228 result in less protuberance than the prior art implants illustrated in FIGS. 1-11 when implanted in bone, because rather than being orthogonal to each other they are directed at angles that result in a more rounded bridge. In addition, the bridge 205 is wider than the legs 201-204, such that the implant 210 would be stronger in bending for the same dimension legs than prior a implant 10.

As illustrated in FIG. 13, the leg 201 has an angle of gamma relative to the bridge 205. Similarly, the leg 202 has an angle of delta relative to bridge 205. The legs 203 and 204 are symmetrical to the legs 201 and 202. The angles gamma and delta may be 90 degrees in the converging position 350, however, the angles gamma and delta are typically acute angles less than 90 degrees. If acute, the gamma and delta angles may be the same angle or different angles. The bridge 205 has a bend in the middle that results in angle epsilon between the two sides. As illustrated in FIG. 14, the legs 201-204 when the implant 210 is in the insertion position 300 are and have an angle of gamma relative to the bridge 205, which is approximately 90 degrees. The bridge 205 when the implant 210 is in the insertion position 300 has an angle of theta, which is either 180 degrees or an angle that fits the anatomy of a patient's bones.

It can be seen by FIGS. 13 and 14 that the implant 210 can produce compression in several ways:

Legs 201 through 204 can be perpendicular to bridge 205 in both the insertion and converging shape, while bridge 205 has angle theta during insertion that moves to smaller angle epsilon causing the four legs to move to a converging position.

Legs 201 through 204 can have an orthogonal angle gamma during insertion but move to acute angle delta in the converging position.

A combination of both the bridge bending and the legs moving relative to the bridge.

Figure 15:
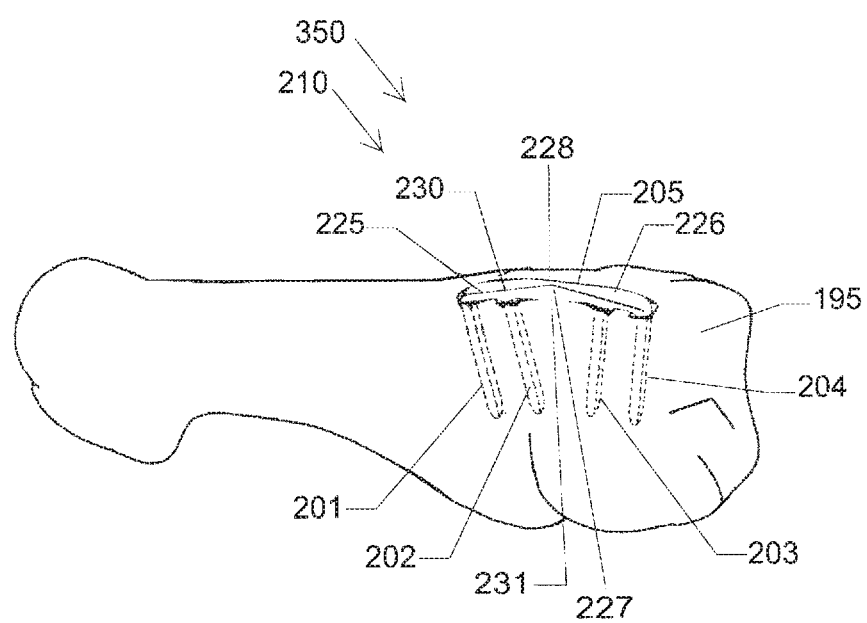
FIG. 15 is a perspective view illustrating the implant according to the first embodiment implanted in a bone.

FIG. 15 shows the implant 210 in bone 20 after implantation. The legs 201-204 are inserted into the bone 195. The bridge 205 is on the surface of the bone 195, however, the bridge 205 has a shape that results in less protuberance than prior art implants. The first, second, third, and fourth surfaces 225-228 form the first upper section 230 that is tapered towards the edges. Unlike prior art implant 10, the implant 210 according to the first embodiment has a more rounded profile when implanted into bone.

Figure 16:
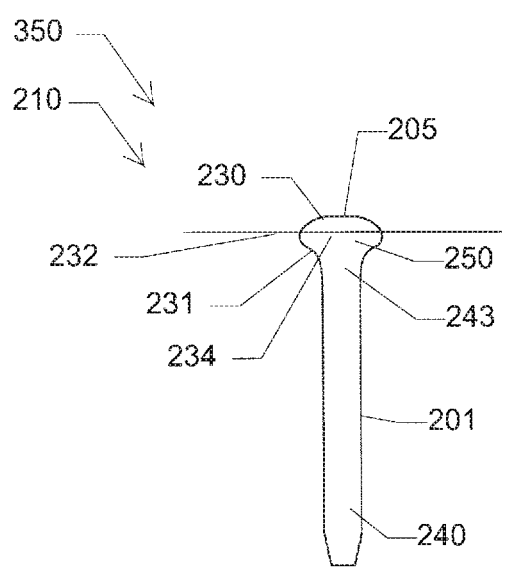
FIG. 16 is an end view illustrating the implant according to the first embodiment.

FIG. 16 shows an end view the implant 210. The legs 201-204 all have a uniform width in this view with tapered ends. It is clear that the legs 201-204 could also be tapered or pointed to better insert into bone. The bridge 205 is non-linear and includes a substantially elliptical shape 250 from the end view. However, as will be discussed herein, because the implant 210 is in the converging position 350, the substantially elliptical shape 250 in this end view results in bridge tapers that are lower profile.

Figure 17:
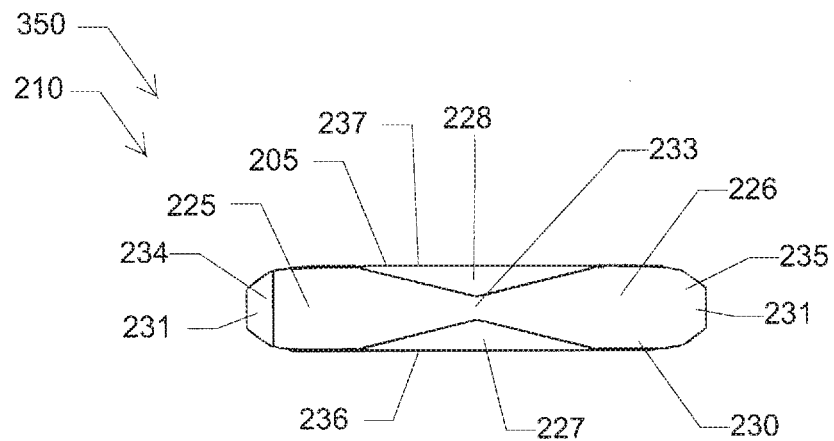
FIG. 17 is a top view illustrating the implant according to the first embodiment.
Figure 18:
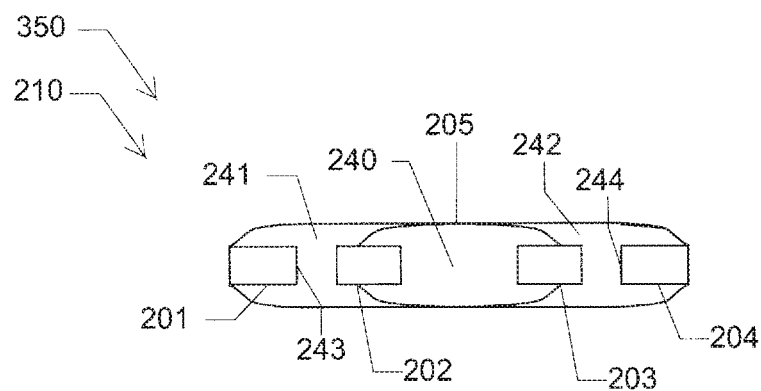
FIG. 18 is a bottom view illustrating the implant according to the first embodiment.

FIGS. 17 and 18 are top and bottom views, respectively, of the implant 10 in the converging position 350. The bridge 205 as shown in FIG. 17 includes the first, second, third, and fourth surfaces 225-228 that are created due to a method of manufacture, which will be described herein. The first, second, third, and fourth surfaces 225-228 taper towards the edges of the implant 210. FIG. 18 shows the four legs 201-204 in their converging shape.

Figure 19:
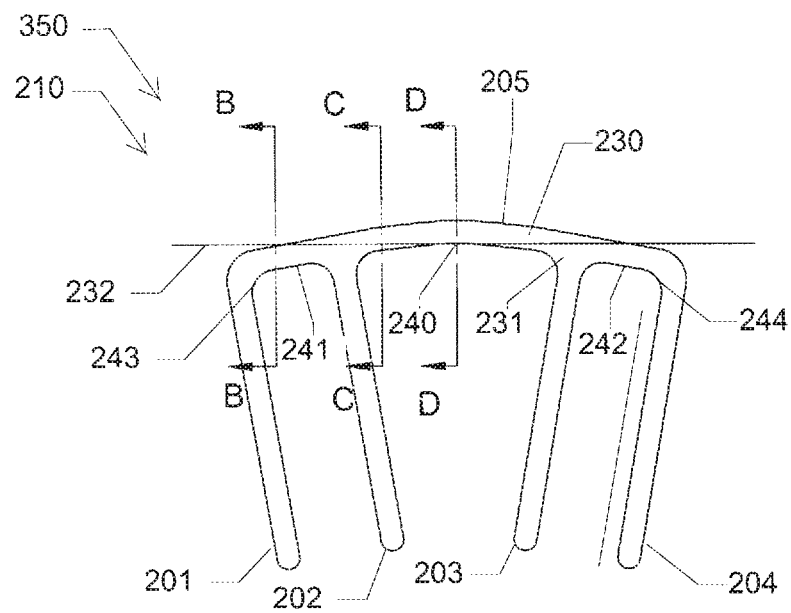
FIG. 19 is a side view illustrating the implant according to the first embodiment with its legs converging.
Figure 20:
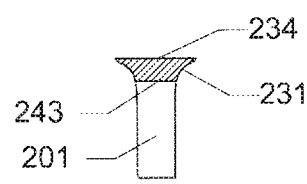
FIG. 20 is cross-sectional side view taken along lines B-B in FIG. 19 illustrating the implant according to the first embodiment.
Figure 21:
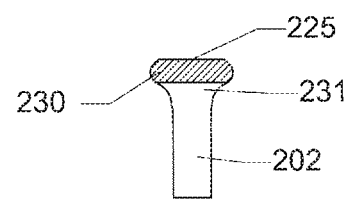
FIG. 21 is cross-sectional side view taken along lines C-C in FIG. 19 illustrating the implant according to the first embodiment.
Figure 22:
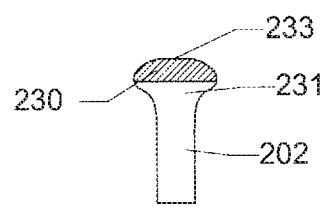
FIG. 22 is cross-sectional side view taken along lines D-D in FIG. 19 illustrating the implant according to the first embodiment.
Figure 23:
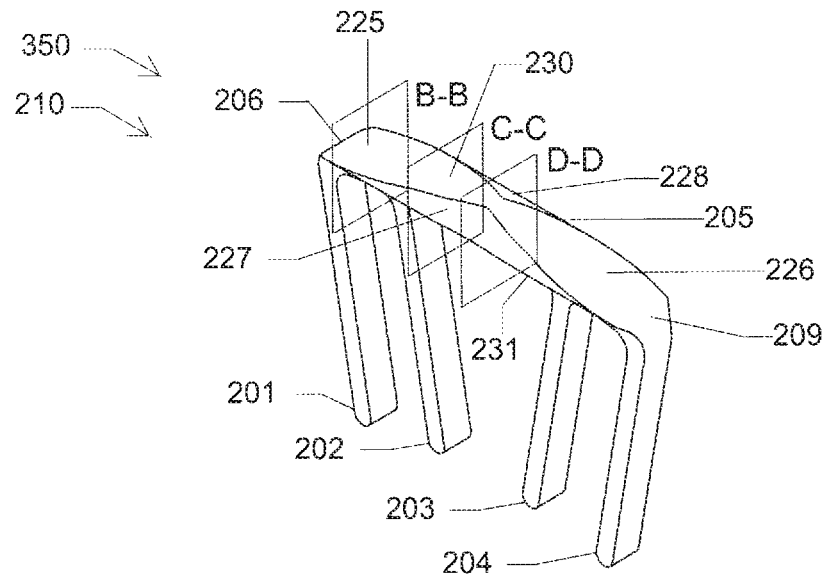
FIG. 23 is a perspective view illustrating the implant according to the first embodiment with its legs converging.
Figure 24:
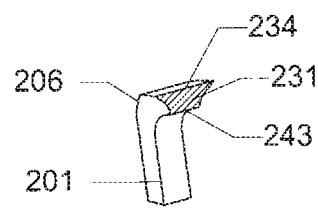
FIG. 24 is cross-sectional side view taken along lines B-B in FIG. 23 illustrating the implant according to the first embodiment.
Figure 25:
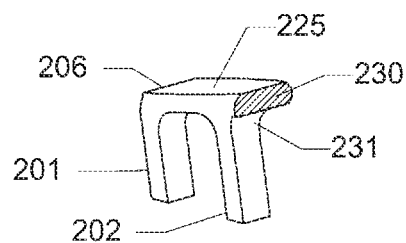
FIG. 25 is cross-sectional side view taken along lines C-C in FIG. 23 illustrating the implant according to the first embodiment.
Figure 26:
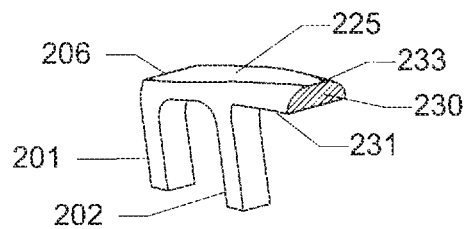
FIG. 26 is cross-sectional side view taken along lines D-D in FIG. 23 illustrating the implant according to the first embodiment.

FIGS. 19 and 23 are side and perspective views of the implant 210 in he converging position 350. FIGS. 20-22 are section views of the bridge 205, taken along lines B-B, C-C, and D-D of FIG. 19. FIGS. 24-26 are section views of the bridge 205, taken along lines B-B, C-C, and D-D of FIG. 23. The section views illustrated in FIGS. 20-22 are taken at the same locations along the bridge 205 as the section views illustrated in FIGS. 24-26. FIGS. 19-26 illustrate that the cross-section of the bridge 205 changes across the length of the bridge 205. The cross-hatched areas shown in FIGS. 20-22 and 24-26 illustrated that at all locations of the bridge 205, the cross section at that location is less than the area and height of the substantially elliptical shape 250 as seen from the end view. Other prior art implants do not have a changing cross section across their connecting bridges. The benefits of the changing cross section is that at all locations of the implant 210, it can lie at a lower profile to bone with tapered upper surfaces.

Figure 27:
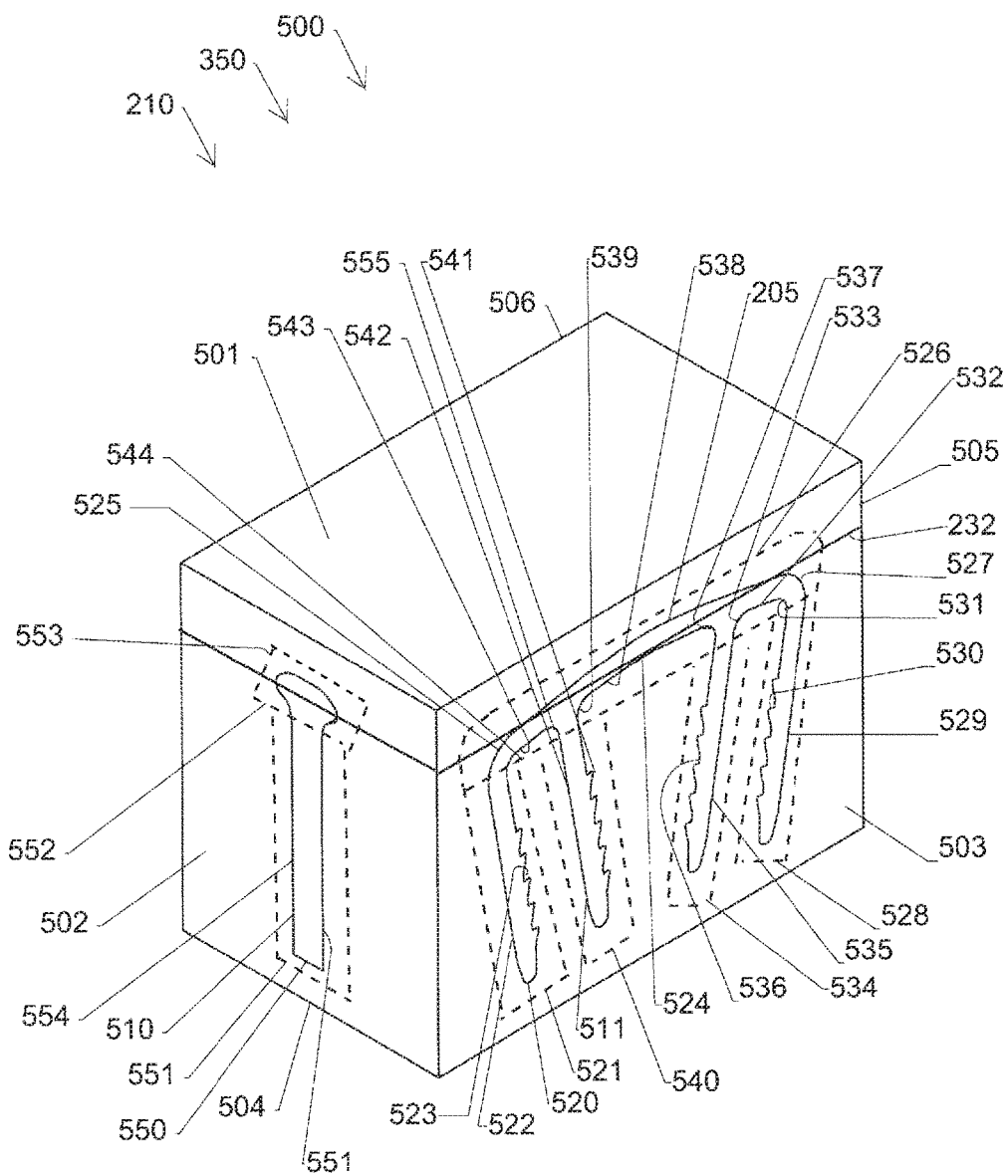
FIG. 27 is a perspective view illustrating a billet of raw material used for cutting the implant according to the first embodiment.

FIG. 27 shows a billet 500 of elastic material, such as shape memory nitinol, that is used to create the implant 210. The billet 500 can be rectangular or square shaped, or any shape that can be conveniently held in machining equipment. The billet 500 has top and bottom surfaces 501 and 504, end surfaces 502 and 505, and front and rear surfaces 503 and 506. In this first embodiment, the billet 500 can be subjected to a variety of manufacturing processes across two surfaces to yield the implant 210. More particularly, the cutting of the billet 500 using manufacturing processes such as rotating mills, saw blades, electric discharge machining, laser machining, or water jets across two surfaces yields the implant 210. In this case, the implant 210 is created by EDM from the surface 503. "Cutting" in the present invention refers to any method of manufacturing that creates a desired shape in a pail and, therefore, is not to be limited to any specific manufacturing method.

The machine traces a path 511 which represents the implant 210 with four barbed legs and the connecting bridge in the converging position 350, the same as FIG. 12. It is noted that the portion of path 511 that becomes the bridge 205 has a uniform thickness across the length of the bridge 205. After the path 511, the machine traces a path 510 from the surface 502 which is an end view like FIG. 17. Alternatively, the paths 510 and 511 could be reversed in sequence. The elements of the manufacturing method consist of:

Cutting the implant 210 in the converging position, which gives the implant designer an option of creating compression in the legs by changing the angle of the bridge, or by changing the angles of the legs relative to the bridge, or both.

Cutting the implant 210 from two perpendicular surfaces with a single continuous path from each surface and the extension of the two paths until they intersect to form the perimeter and profile of the implant 210.

Cutting the implant 210 with path 511 that has a uniform width across the entire bridge 205 of implant 210.

Cutting the implant 210 with the path 510 and the substantially elliptical shape 250 such that the bridge 205 is wider and hence stronger than an implant with uniform width.

Some of the benefits of the manufacturing method shown in FIG. 27 include a resulting implant 210 that has tapered first, second, third, and fourth surfaces 225-228 on the bridge 205. The bridge 205 is also wider than prior art implants, resulting in more bending strength. The bridge 205 has a non-uniform cross section from end to end, with all points along the bridge lower in profile than the substantially elliptical shape 250.

The following is an example illustrating the production of an implant 210 from a billet 500 and is presented to aid in the understanding of the manufacturing method shown in FIG. 27. It should be understood that the steps of operation as well as the location, direction, and order of the cuts and paths may be varied and that the manufacturing method is not limited to the below specific example. Illustratively, the implant 210 may be produced using a single continuous cut of the paths 511 and 510. Alternatively, the cutting along the paths 511 and 510 may be discrete in that the bridge 205 may be cut completely either before or after each of the legs 201-204 are cut.

A cutting machine begins at point 520 and traces the path 511. In particular, the machine follows an outer side leg path 522 of a leg path 521 and cuts an outer side portion of the leg 201. At the end of the outer side leg path 522, the machine transitions to a second lower section path 524 and follows an outer corner path 525 of the second lower section path 524 to cut an outer portion of the corner 206. The machine transitions from the outer corner path 525 of the second lower section path 524 to a first upper section path 526 at the first end transition 234 as defined by the plane 232. Following the first upper section path 526, the machine cuts the central surface 233, the first surface 225, and the second surface 226 of the first upper section 230 that lies between the first end transition 234 and the second end transition 235. The first upper section path 526 is non-linear in that it follows an arc between the first end transition 234 and the second end transition 235, although the arc may flatten at the central surface 226 to provide a flattened profile of the bridge 205 at the central surface 226. The non-linear shape of the first upper section path 526 ensures the removal of material between a plane tangent to the central surface 226 and the first and second surfaces 225 and 226 such the bridge 205 presents a profile lower than bridges with a linear profile. At the second end transition 235 as defined by the plane 232, the machine transitions to the second lower section path 524 and follows an outer corner path 527 of e second lower section path 524 to cut an outer portion of the corner 209. The machine transitions from the outer corner path 527 of the second lower section path 524 to a leg path 528 and follows outer side leg path 529 and an inner side leg path 530 to cut outer and inner side portions of the leg 209. At the end of inner side leg path 530, the machine transitions to the second lower section path 524 and follows an inner corner path 531 of the second lower section path 524 to cut an inner portion of the corner 209. Once the end of the inner corner path 531 of the second lower section path 524 is reached, the machine follows a second surface path 532 of the second lower section path 524 to cut the second surface 242. At the end of the second surface path 532 of the second lower section path 524, the machine follows a corner path 533 of the second lower section path 524 to cut the corner 216. The machine transitions from corner path 533 of the second lower section path 524 to a leg path 534 and follows an outer side leg path 535 and an inner side leg path 536 to cut outer and inner side portions of the leg 203. At the end of inner side leg path 536, the machine transitions to the second lower section path 524 and follows a corner path 537 of the second lower section path 524 to cut the corner 208. After reaching the end of the corner path 537 of the second lower section path 524, the machine follows a central surface path 538 of the second lower section path 524 to cut the central surface 240. At the end of the central surface path 538 of the second lower section path 524, the machine follows a corner path 539 of the second lower section path 524 to cut the corner 207. The machine transitions from corner path 539 of the second lower section path 524 to a leg path 540 and follows an inner side leg path 541 and an outer side leg path 542 to cut outer and inner side portions of the leg 202. At the end of outer side leg path 542, the machine transitions to the second lower section path 524 and follows a corner path 555 of the second lower section path 524 to cut the corner 215. Once the end of the corner path 555 of the second lower section path 524 is readied, the machine follows a first surface path 543 of the second lower section path 524 to cut first surface 241. After reaching the end of first surface path 543 of the second lower section path 524, the machine then transitions to an inner corner path 544 of the second lower section path 524 to cut an inner portion of the corner 206. The machine transitions from the inner corner path 544 of the second lower section path 524 to the leg path 528 and follows an inner side leg path 523 until the point 520 to cut an inner side portion of the leg 201. Although the legs paths 528 and 540 interrupt the second lower section path 524, it should be understood that the first surface path 543, the second surface path 532, and the central surface path 538 are non-linear in that they are aligned to follow an arc between the first and second leg transitions 243 and 244, although the arc may increase at the central surface 240 to provide a reduced profile of the bridge 205 at the central surface 240. The non-linear shape of the second lower section path 524 ensures the removal of material between a plane intersecting the legs 201-204 and the first surface 241, the second surface 242, and the central surface 240 such the bridge 205 presents a profile lower than bridges with a linear profile.

The cutting machine begins at point 550 and traces the path 510. In particular, the machine follows a first face leg path 551 of a leg path 551 and cuts first face portions of the legs 201-204. At the end of first face leg path 551, the machine transitions to a second lower section path 552 to cut a portion of the second lower section 231. The machine transitions from the second lower section path 552 to a first upper section path 553 at the first side transition 236 as defined by the plane 232. Following the first upper section path 553, the machine cuts the central surface 233, the third surface 227, and the fourth surface 228 of the first upper section 230 that lies between the first side transition 236 and the second end transition 237. At the second side transition 237 as defined by the plane 232, the machine transitions to the second lower section path 552 and cuts a portion of the second low section 231. The machine transitions from the second lower section path 552 to the leg path 551 and follows a first face leg path 554 until the point 550 to cut second face portions of the legs 201-204. Although the leg path 551 interrupts the second lower section path 552, it should be understood that the second lower section path 552 and the first upper section path 553 are non-linear in that they define the substantially elliptical shape 250. As such, the first upper section path 553 is non-linear in that it follows an arc substantially along an ellipse between the first side transition 236 and the second side transition 237, although the arc may flatten at the central surface 226 to provide a flattened profile of the bridge 205 at the central surface 226. The non-linear shape of the first upper section path 553 ensures the removal of material between a plane tangent to the central surface 226 and the third and fourth surfaces 225 and 226 such that bridge 205 presents a profile lower than bridges with a linear profile. Furthermore, the second lower section path 552 is non-linear in that it follows an arc substantially along an ellipse between the first side transition 236 and the second side transition 237. The non-linear shape of the second lower section path 524 ensures the second lower section 231 is wider than the legs 201-204 in order to provide the implant 210 with increased bending strength.

From the foregoing, it should be understood that producing the implant 210 from the billet 500 using a method of manufacture wherein two intersecting non-linear paths are cut from two different directions results in the bridge 205 of implant 210 having a smooth reduced profile composite surface and a non-uniform cross-sectional area. In particular, cutting the non-linear first upper section path 526 and the non-linear second lower section path 524 from a first direction relative to the billet 500 and cutting the non-linear first upper section path 553 and the non-linear second lower section path 552 from a second direction relative to the billet 500 creates the implant 210 having a bridge 205 with tapered first, second, third, and fourth surfaces 225-228. Moreover, the bridge 205 includes a non-uniform cross-sectional area as illustrated in FIGS. 20-22 and 24-26. As such, the implant 210 includes a low profile and provides less of protuberance to a patient as well as increased bending strength.

Figure 28:
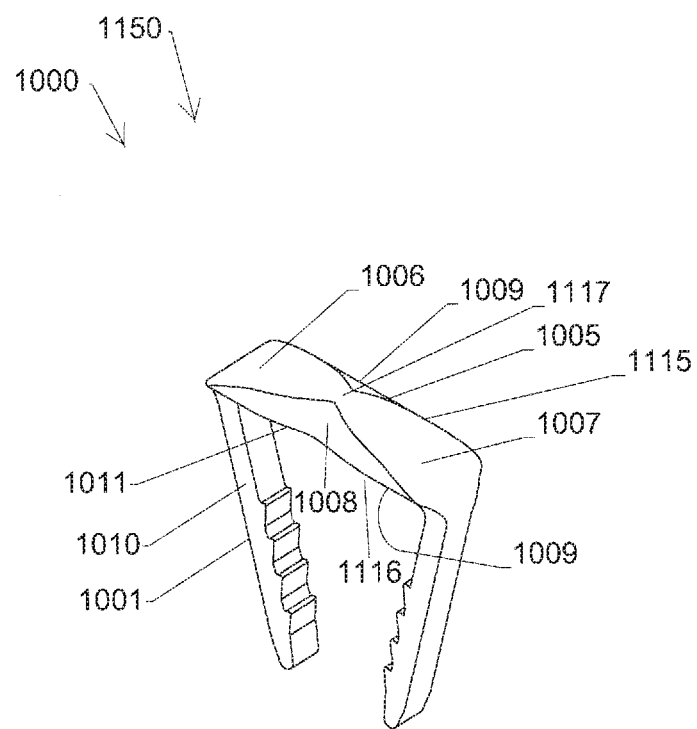
FIG. 28 is a perspective view illustrating an implant according to a second embodiment with its legs converging.

FIG. 28 illustrates an implant 1000 according to a second embodiment. The implant 1000 is shown in a converging position 1150. The implant 1000 includes legs 1001 and 1002 connected by a bridge 1005. The implant 1000 is a two-legged version of implant 210 such that the legs 1001 and 1002 are substantially identical to the legs 201 and 204 of the implant 210 and the bridge 1005 is substantially identical to the bridge 205. The bridge 1005 includes a first upper section 1115, which is substantially identical to the first upper section 230, and a second lower section 1116, which is substantially identical to the second lower section 231. The first upper section 1115 includes a central surface 1117 and first, second, third, and fourth surfaces 1006-1009, which are substantially identical the central surface 233 and the first, second, third, and fourth surfaces 225-228. The second lower section 1116 includes a central surface 1010 and first and second surfaces 1011 and 1012, which are substantially similar to the central surface 240 and the first and second surfaces 241 and 242, with the exception that the second lower surface 1116 presents a continuous, uninterrupted surface due to the elimination of interior legs 202 and 203. Similar to the implant 210, the implant 1000 has in an insertion position, where the legs 1001 and 1002 are substantially parallel. Substantially the same as the implant 210, the implant 1000 creates compression from either a bend in the bridge 1005, the changing the angles of the legs 1001-1002 relative to the bridge 1005, or a combination of both.

Figure 29:
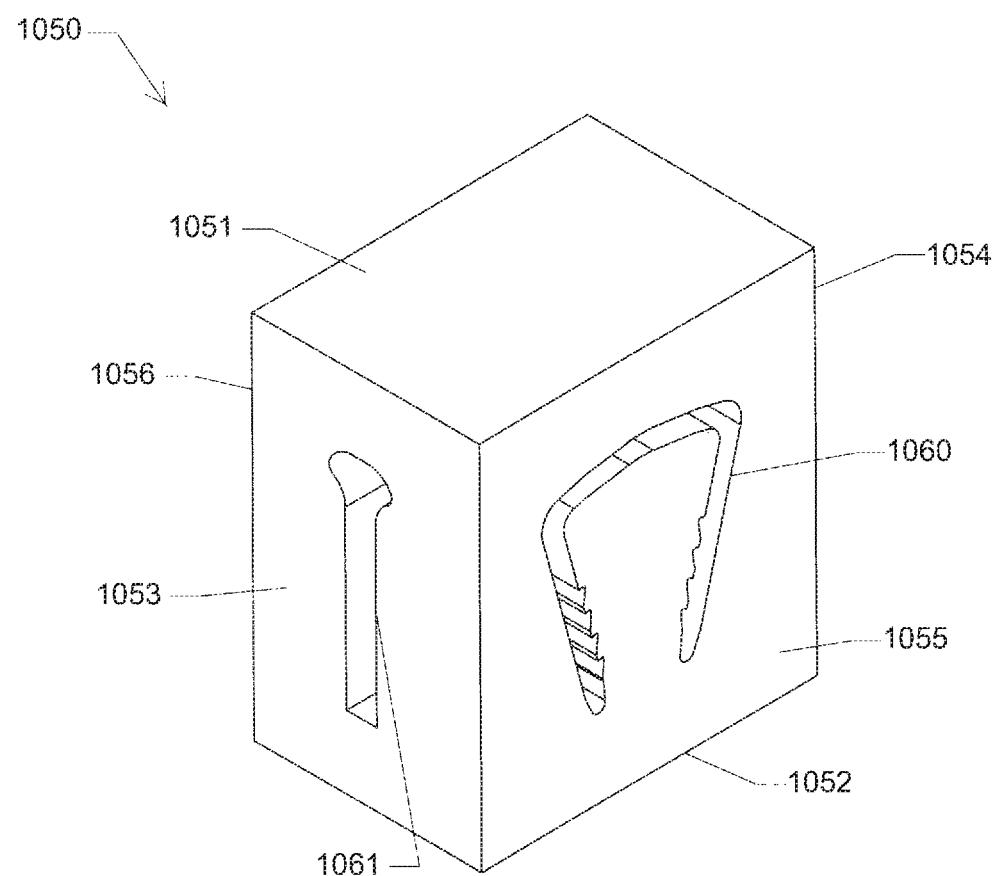
FIG. 29 is a perspective view illustrating a billet of raw material used for cutting the implant according to the second embodiment.
Figure 30:
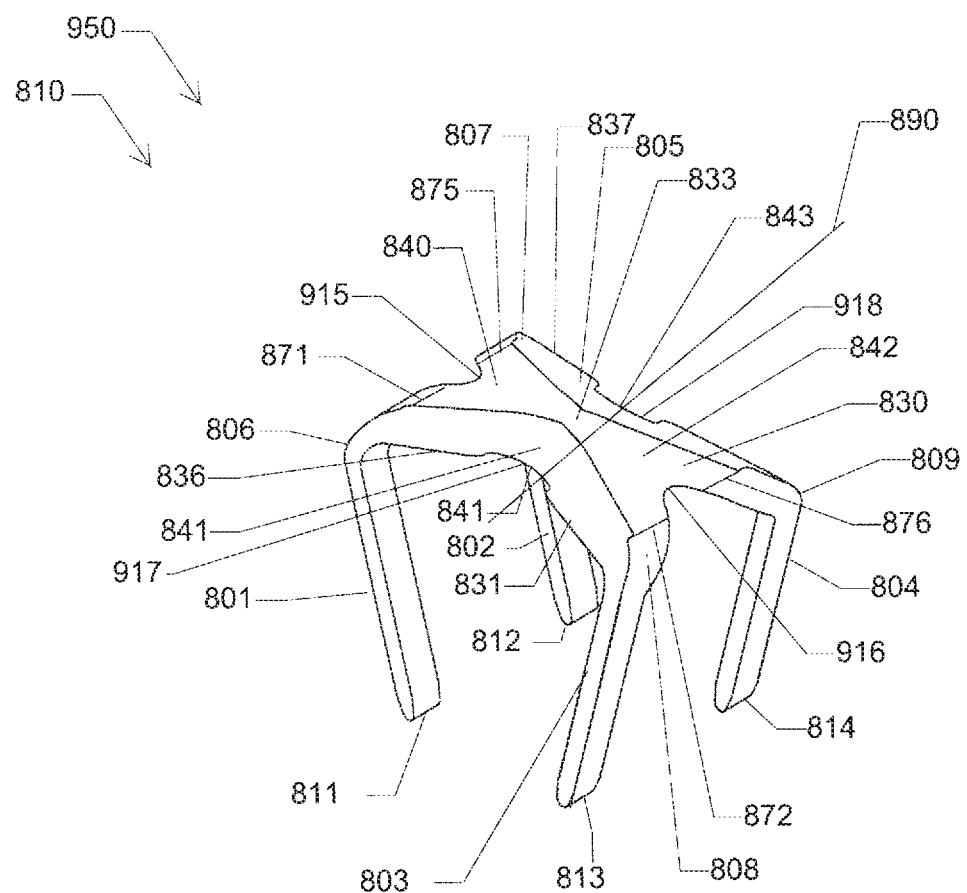
FIGS. 30 and 31 are a perspective views illustrating an implant according to a third embodiment with its legs converging.

FIG. 29 shows a billet 1050 of elastic material, such as shape memory nitinol, that is used to create the implant 1000. The billet 1050 can he rectangular or square shaped, or any shape that can be conveniently held in machining equipment. The billet 1050 has top and bottom surfaces 1051 and 1052, end surfaces 1053 and 1054, and front and rear surfaces 1055 and 1056. In this second embodiment, the billet 1050 can be subjected to a variety of manufacturing processes across two surfaces to yield the implant 1000. More particularly, the cutting of the billet 1050 using manufacturing processes such as rotating mills, saw blades, electric discharge machining, laser machining, or water jets across two surfaces yields the implant 1000. In this case, the implant 1000 is created by EDM from the surface 1055. "Cutting" in the present invention refers to any method of manufacturing that creates a desired shape in a part and, therefore, is not to be limited to any specific manufacturing method.

The machine traces a path 1060 which represents the implant 1000 with two barbed legs and the connecting bridge in the converging position, the same as FIG. 29. It is noted that the portion of path 1060 that becomes the bridge 1005 has a uniform thickness across the length of the bridge 1005. After the path 1060, the machine traces a path 1061 from the surface 1053. The method of manufacturing the implant 1000 is substantially similar to the implant 210, with the path 1061 being identical to the path 510 and the path 1060 being substantially similar to the path 511 except that the second lower surface 1116 presents a continuous, uninterrupted surface due to the elimination of interior legs 202 and 203.

FIGS. 30-42 illustrate a third embodiment of an implant 810. The implant 810 is shown in a converging position 950. The implant 810 can be made from any elastic material. An example of such a material is a shape memory implant made from nitinol. The implant 810 includes legs 801-804 connected by a bridge 805. The implant 810 includes corners 806-809 that connect a respective leg 801-804 with the bridge 805. Each leg 801-804 has a respective tip 811-814. The legs 801-804 are smooth; however, it is possible to include barbs on legs 801-804 to improve the pull-out resistance of the implant 810. In the third embodiment, the corners 806-809 store energy when deformed and create a compressive force that moves tips 811-814 angularly between 0 degrees and 90 degrees relative to the central axis 890. Illustratively, the tips 811-814 may move perpendicular (90 degrees) relative to the central axis 890 such that the linear distance between the tips 811 and 813 and the tips 812 and 814 decreases while the linear distance between the tips 811 and 812 and the tips 813 and 814 remains constant. Conversely, the tips 811-814 may move parallel (0 degrees) relative to the central axis 890 such that the linear distance between the tips 811 and 812 and the tips 813 and 814 decreases while the linear distance between the tips 811 and 813 and the tips 812 and 814 remains constant. Finally, the tips 811-814 may move at an angle between parallel (0 degrees) and perpendicular (90 degrees) relative to the central axis 890 such that the linear distances between each of the tips 811-814 decreases. In the third embodiment, the implant 810 may create compression from a bend in the bridge 805, the changing the angles of the legs 801-804 relative to the bridge 805, or a combination of both.

The bridge 805 includes a first upper section 830 and a second lower section 831. The first upper section 830 is the top portion of the bridge 805 between the corners 806-809, and the second lower section 831 is the underside portion of the bridge 805 between the corners 806-809. The first upper section 830 includes a central surface 833 and first, second, third, and fourth surfaces 840-843. The central surface 833 may be linear to lower the profile of the first upper section 830. Alternatively, the central surface 833 may be non-linear to provide a smooth transition from the central surface 833 to each of the first, second, third, and fourth surfaces 840-843.

The first surface 840 is non-linear and tapers from the central surface 833 to a first end transition 871 located at the corner 806 and a second end transition 875 located at the corner 807. In the third embodiment, the first surface 840 includes a non-linear end portion 915 created at the end of the first surface 840 between the corners 806 and 807 during the manufacture of the implant 810. The second surface 842 is non-linear and tapers from the central surface 833 to a third end transition 872 located at the corner 808 and a fourth end transition 876 located at the corner 809. In the third embodiment, the second surface 842 includes a non-linear end portion 916 created at the end of the second surface 842 between the corners 806 and 807 during the manufacture of the implant 810. The first, second, third, and fourth end transitions 871, 872, 875, and 876 are between the first upper section 830 and the second lower section 831. The third surface 841 is non-linear and tapers from the central surface 833 to a first side transition 836 between the first upper section 830 and the second lower section 831. In the third embodiment, the third surface 841 includes a non-linear side portion 917 created in a central portion of the third surface 841 at the first side transition 836 during the manufacture of the implant 810. The fourth surface 843 is non-linear and tapers from the central surface 833 to a second side transition 837 between the first upper section 830 and the second lower section 831. In the third embodiment, the fourth surface 843 includes a non-linear side portion 918 created in a central portion of the fourth surface 843 at the second side transition 837 during the manufacture of the implant 810. The first, second, third, and fourth surfaces 841-843 in the third embodiment each taper from the central surface 833 at an angle of between 5 degrees and 85 degrees when measured from a plane tangent to the central surface 833. The tapering of the first, second, third, and fourth surfaces 841-843 from the central surface 833 provides the implant 810 with a first upper section 830 that has a smooth composite surface and a non-uniform cross-sectional thickness between the first, second, third, and fourth end transitions 871-874 as illustrated in FIGS. 34-36 and 38-40. As a result, the implant 810 includes a low profile and provides less of protuberance to a patient.

The second lower section 831 includes a central surface 880, a first surface 881, a second surface 882, a third surface 883, and a fourth surface 884. The central surface 880 is non-linear to provide a smooth transition from the central surface 880 to each of the first, second, third, and fourth surfaces 881-884. As described more fully herein with reference to FIGS. 32 and 42, the non-linear end portions 915 and 916 and the non-linear side portions 917 and 918 are created during manufacture of the central surface 880. The first surface 881 is non-linear and tapers from the central surface 880 to a first leg transition 837 located at the corner 806 and a second leg transition 894 located at the corner 807. The second surface 882 is non-linear and tapers from the central surface 833 to a third leg transition 895 located at the corner 808 and a fourth leg transition 896 located at the corner 809. The first, second, third, and fourth leg transitions 893, 894, 895, and 896 are between the first upper section 830 and the second lower section 831. The third surface 883 is non-linear and tapers from the central surface 880 to a first side transition 888 between the first upper section 830 and the second lower section 831. The fourth surface 884 is non-linear and tapers from the central surface 880 to a second side transition 889 between the first upper section 830 and the second lower section 831.

In the third embodiment, the first, second, third, and fourth surfaces 881-884 each taper from the central surface 880 at an angle of between 5 degrees and 85 degrees when measured from a plane tangent to the central surface 880. The tapering of the first, second, third, and fourth surfaces 881-884 from the central surface 880 provides the implant 810 with a second lower section 831 that has a smooth composite surface and a non-uniform cross-sectional thickness between the first, second, third, and fourth leg transitions 893-896 as illustrated in FIGS. 34-36 and 38-40. As a result, the implant 810 includes a low profile and provides less of protuberance to a patient.

Figure 31:
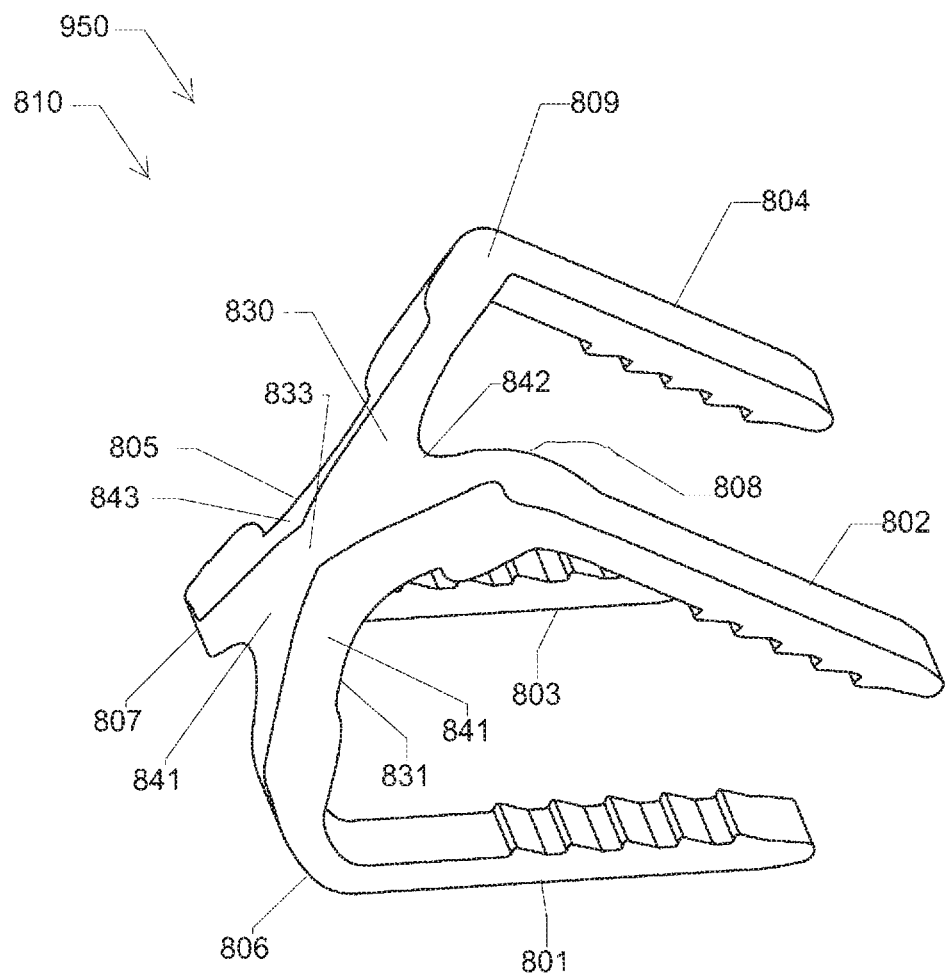

FIG. 31 illustrates the implant 810 in the converging position 950 and with barbs on legs 801-804. In the converging position 950, each of the legs 801-804 has an acute angle of less than 90 degrees relative to the bridge 805. The implant 810 also has an insertion position that allows the implant 810 to be inserted into bone. In the insertion position, each of the legs 801-804 are substantially parallel such that the legs 801-804 have an angle of approximately 90 degrees relative to the bridge 805. The bridge 805 has a bend in the middle that results in angle of less than 180 degrees between the two sides. The bridge 205 when the implant 210 is in the insertion position 300 has an angle, which is either 180 degrees or an angle that fits the anatomy of a patient's bones.

In the converging position 950, the bridge 805 has been manufactured such that there are tapers on bridge 805 towards the edges of the bridge, labeled as first, second, third, and fourth surfaces 840-843. The first, second, third, and fourth surfaces 840-843 result in less protuberance than the prior art implants when implanted in bone, because rather than being orthogonal to each other they are directed at angles that result in a more rounded bridge. In addition, the bridge 805 is wider than the legs 801-804, such that the implant 810 would be stronger in bending for the same dimension legs than prior art implant 10.

Figure 32:
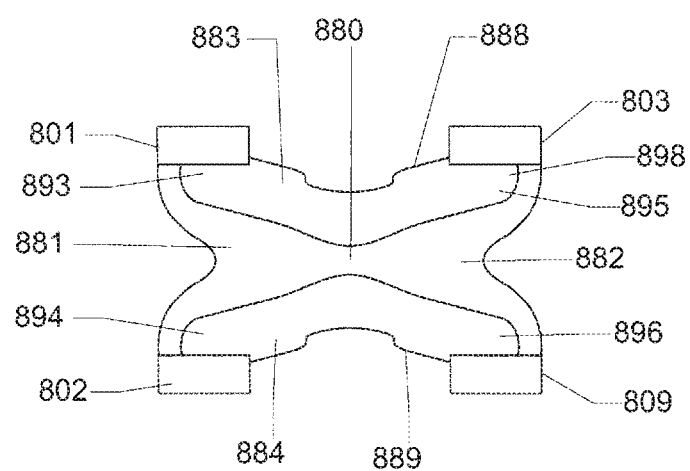
FIG. 32 is a bottom view illustrating the implant according to the third embodiment.

FIG. 32 is a bottom view of the implant 810 in the converging position 950. The bridge 805 includes the central surface 880 and the first, second, third, and fourth surfaces 881-884 that are created due to a method of manufacture, which will be described herein. The first, second, third, and fourth surfaces 881-884 taper towards the edges of the implant 810.

Figure 33:
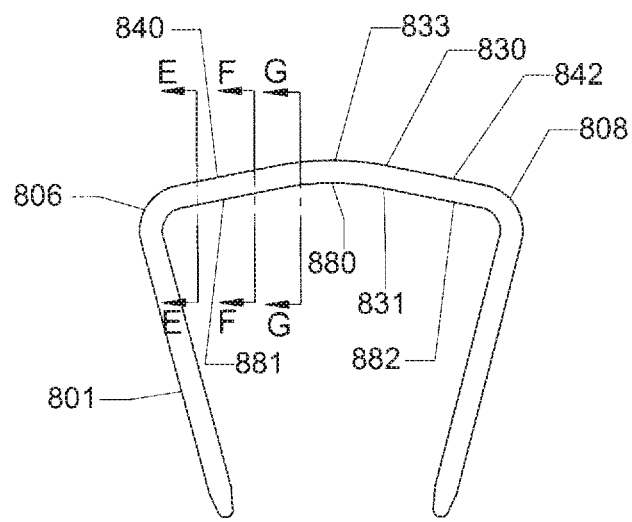
FIG. 33 is a side view illustrating the implant according to the third embodiment with its legs converging.
Figure 34:
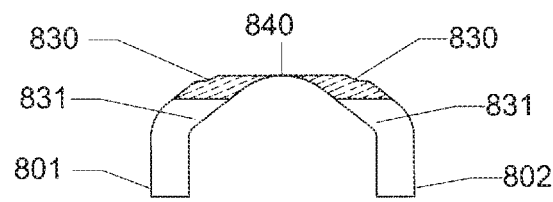
FIG. 34 is cross-sectional side view taken along lines E-E in FIG. 34 illustrating the implant according to the third embodiment.
Figure 35:
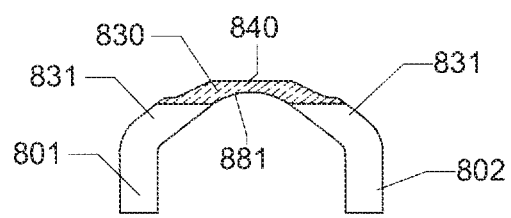
FIG. 35 is cross-sectional side view taken along lines F-F in FIG. 34 illustrating the implant according to the third embodiment.
Figure 36:
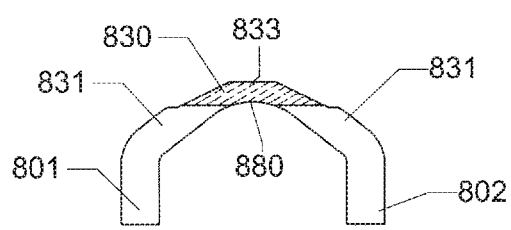
FIG. 36 is cross-sectional side view taken along lines G-G in FIG. 34 illustrating the implant according to the third embodiment.
Figure 37:
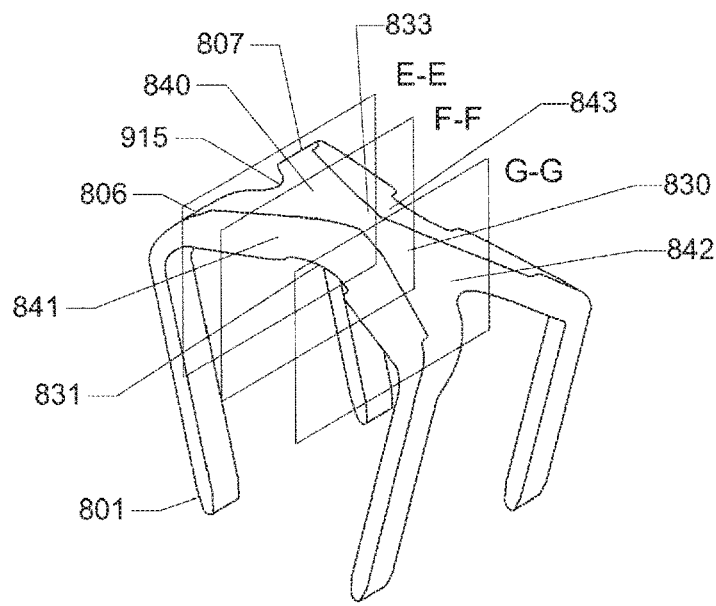
FIG. 37 is a perspective view illustrating the implant according to the third embodiment with its legs converging.
Figure 38:
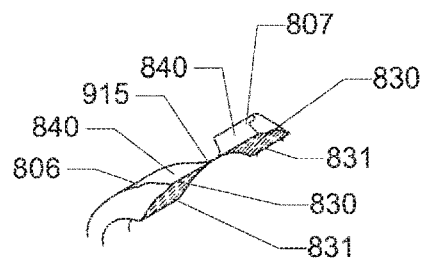
FIG. 38 is cross-sectional side view taken along lines E-E in FIG. 37 illustrating the implant according to the third embodiment.
Figure 39:
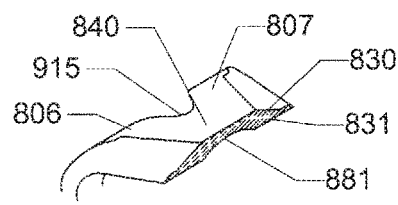
FIG. 39 is cross-sectional side view taken along lines F-F in FIG. 37 illustrating the implant according to the third embodiment.
Figure 40:
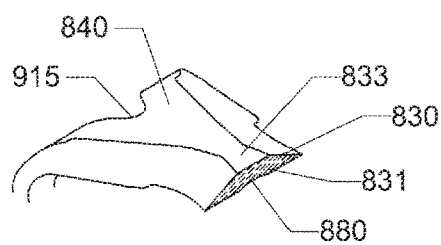
FIG. 40 is cross-sectional side view taken along lines G-G in FIG. 37 illustrating the implant according to the third embodiment.

FIGS. 33 and 37 are side and perspective views of the implant 810 in the converging position 950. FIGS. 34-36 are section views of the bridge 805, taken along lines E-E, F-F, and G-G of FIG. 33. FIGS. 38-40 are section views of the bridge 805, taken along lines E-E, F-F, and G-G of FIG. 37. The section views illustrated in FIGS. 34-36 are taken at the same locations along the bridge 805 as the section views illustrated in FIGS. 38-40. FIGS. 33-40 illustrate that the cross-section of the bridge 805 changes across the length of the bridge 805. The cross-hatched areas shown in FIGS. 34-36 and 38-40 illustrate that at all locations of the bridge 805, the cross section at that location is less than the area and height of the bridge 805 when viewed at an end. Other prior art implants do not have a changing cross-section across their connecting bridges. The benefits of the changing cross-section is that at all locations of the implant 810, it can lie at a lower profile to bone with tapered upper surfaces.

Figure 41:
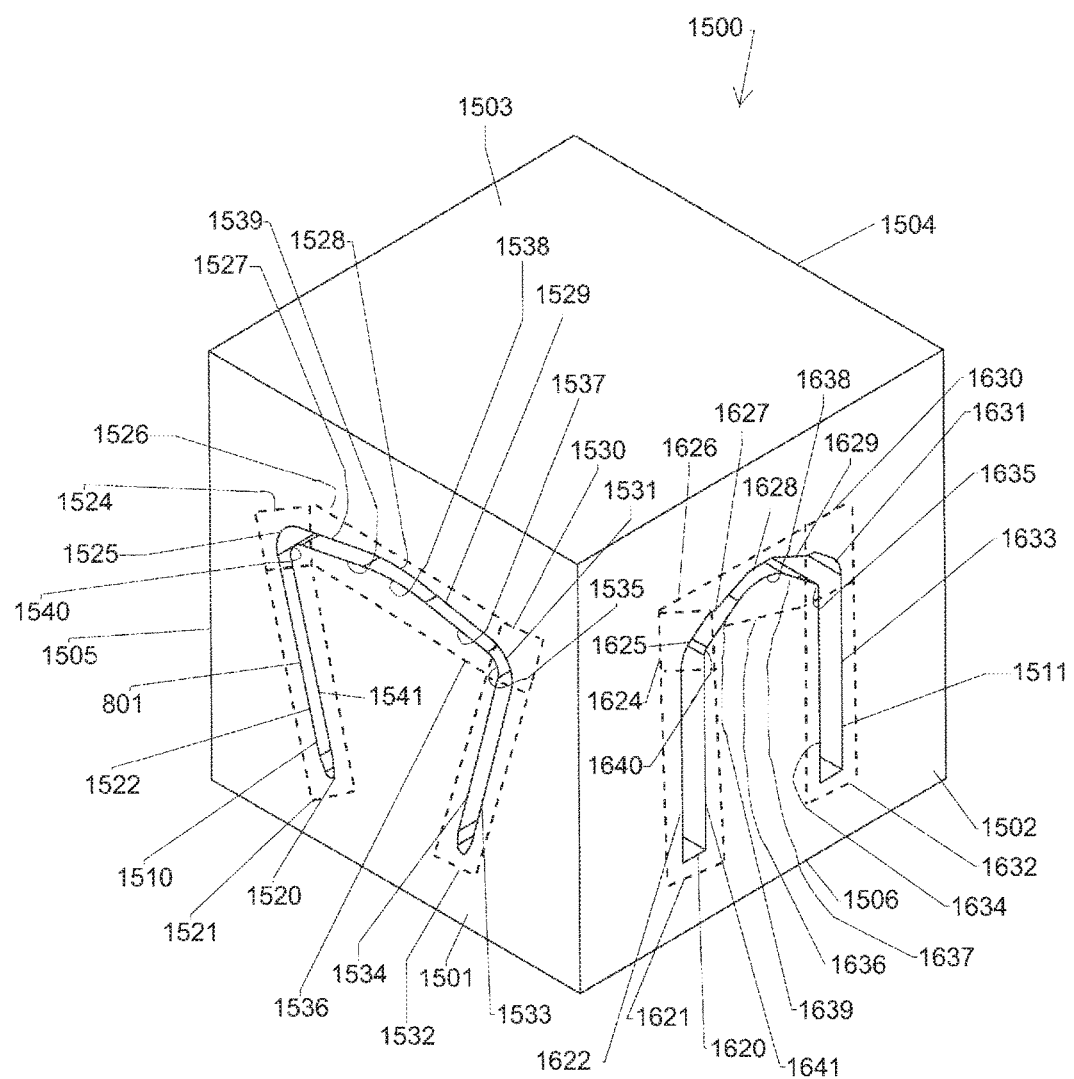
FIGS. 41 and 42 are perspective views illustrating a billet of raw material used for cutting the implant according to the third embodiment.

FIG. 41 shows a billet 1500 of elastic material, such as shape memory nitinol, that is used to create the implant 810. The billet 1500 can be rectangular or square shaped, or any shape that can be conveniently held in machining equipment. The billet 1500 has top and bottom surfaces 1503 and 1506, end surfaces 1502 and 1505, and front and rear surfaces 1501 and 1504. In this third embodiment, the billet 1500 can be subjected to a variety of manufacturing processes across two surfaces to yield the implant 810. More particularly, the cutting of the billet 1500 using manufacturing processes such as rotating mills, saw blades, electric discharge machining, laser machining, or water jets across two surfaces yields the implant 810. In this case, the implant 810 is created by EDM from the surface 1501. "Cutting" in the present invention refers to method of manufacturing that creates a desired shape in a part and, therefore, is not to be limited to any specific manufacturing method.

The machine traces a path 1510 from the surface 1501, which rrepresents the implant 810 in the converging position 950. After the path 1510, the machine traces a path 1511 from the surface 1502. Alternatively, the paths 1510 and 1511 could be reversed in sequence. The elements of the manufacturing method consist of:

Cutting the implant 810 in the converging position, which gives the implant designer an option of creating compression in the legs by changing the angle of the bridge, or by changing the angles of the legs relative to the bridge, or both.

Cutting the implant 810 from two perpendicular surfaces with a single continuous path from each surface.

Cutting the implant 810 with path 1510, wherein the path 1510 has a uniform separation around the path.

Cutting the implant 810 with the path 1511 such that the bridge 805 of resultant implant 810 is wider and hence stronger than an implant with width equal to the width of the legs.

Some of the benefits of the manufacturing method shown in FIG. 41 include a resulting implant 810 that has tapered first, second, third, and fourth surfaces 840-843 on the bridge 805. The bridge 805 is also wider than prior art implants, resulting in more bending strength. The bridge 805 has anon-uniform cross section from end to end, with all points along the bridge lower in profile than either paths 1510 and 1511.

Figure 42:
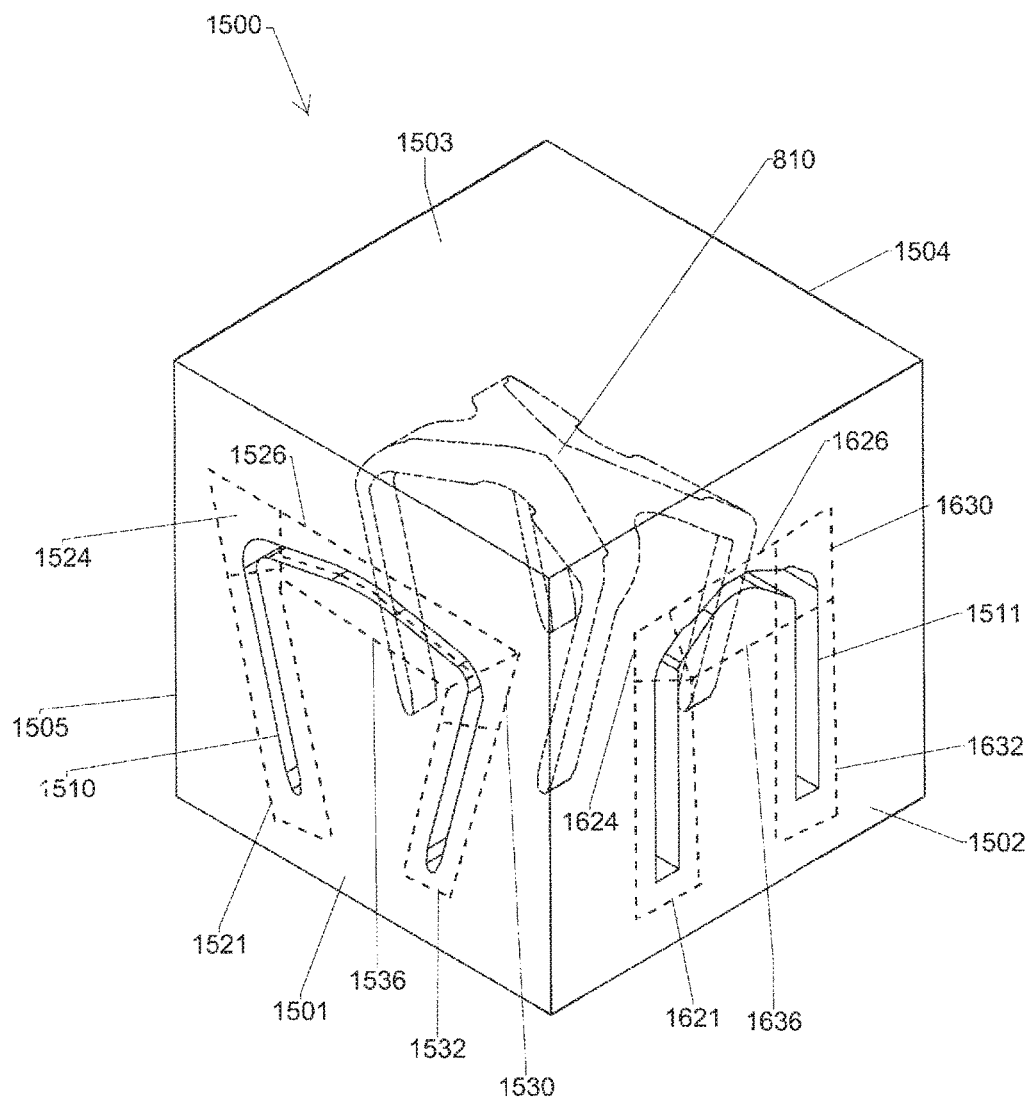

The following is an example illustrating the production of an implant 810 from a billet 1500 and is presented to aid in the understanding of the manufacturing method shown in FIGS. 41 and 42. It should be understood that the steps of operation as well as the location, direction, and order of the cuts and paths may be varied and that the manufacturing method is not limited to the below specific example. Illustratively, the implant 810 may be produced using a single continuous cut of the paths 1510 and 1511. Alternatively, the cutting along the paths 1510 and 1511 may be discrete in that the bridge 805 may be cut completely either before or after each of the legs 801-804 are cut.

A cutting machine begins at point 1520 and traces the path 1510. In particular, the machine follows an outer side leg path 1522 of a leg path 1521 and cuts an outer side portion of the legs 801 and 802. At the end of the outer side leg path 1522, the machine transitions to a first corner set path 1524 and follows an outer corner path 1525 to cut an outer end portion of the corners 806 and 807. The machine transitions from the outer corner path 1525 to an end upper section path 1526 at the first end transitions 871 and 875. In the third embodiment, the end upper section path 1526 includes a first surface path 1527, a central surface path 1528, and a second surface path 1529. Following each of the first surface path 1527, the central surface path 1528, and the second surface path 1529 of the end upper section path 1526, the machine cuts the first surface 840, a portion of the central surface 833, and the second surface 842 of the first upper section 830 that lies between the end transitions 871 and 875 and the end transitions 872 and 876. The end upper section path 1526 is non-linear in that it follows an arc between the end transitions 871 and 875 and the end transitions 872 and 876. In particular, the first surface path 1527, the central surface path 1528, and the second surface path 1529 have a substantially similar arc radius in that the first surface path 1527, the central surface path 1528, and the second surface path 1529 follow a substantially uniform arc along the entire length of the end upper section path 1526, although the arc may flatten at the central surface 833 to provide a flattened profile of the bridge 805 at the central surface 833. The non-linear shape of the end upper section path 1526 ensures the removal of material between a plane tangent to the central surface 833 and the first and second surfaces 840 and 842 such the bridge 805 presents a profile lower than bridges with a linear profile. At the end transitions 872 and 876, the machine transitions to a second corner set path 1530 and follows an outer corner path 1531 to cut an outer end portion of the corners 808 and 809. The machine transitions from the outer corner path 1531 to a leg path 1532 and follows an outer side leg path 1533 and an inner side leg path 1534 to cut outer and inner side portions of the legs 803 and 804. At the end of inner side leg path 1534, the machine transitions to the second corner set path 1530 and follows an inner corner path 1535 to cut an inner end portion of the corners 808 and 809. The machine transitions from the inner corner path 1535 to an end lower section path 1536 at the third and fourth leg transitions 895 and 896. In the third embodiment, the end lower section path 1536 includes a first surface path 1539, a central surface path 1538, and a second surface path 1537. Following, the second surface path 1537, the central surface path 1538, and the first surface path 1539 of the end lower section path 1536, the machine cuts the second surface 881, a portion of the central surface 880, and the first surface 882 of the second lower section 831 that lies between the third and fourth leg transitions 895 and 896 and the first and second leg transitions 893 and 894. The end lower section path 1536 is non-linear in that it follows an arc between the third and fourth leg transitions 895 and 896 and the first and second leg transitions 893 and 894. In a first path configuration, the first surface path 1539, the central surface path 1538, and the second surface path 1537 have a substantially similar arc radius in that the first surface path 1539, the central surface path 1538, and the second surface path 1537 follow a substantially uniform arc along the entire length of the end lower section path 1536, although the arc may flatten at the central surface 880 to provide a flattened profile of the bridge 805 at the central surface 880. In an alternative path configuration according to the third embodiment, the first surface path 1539 and the second surface path 1537 have a substantially similar arc radius and follow a substantially symmetrical and uniform arc. The central surface path 1538, however, has an arc radius that is smaller than the arc radii of the first and second surface paths 1539 and 1537. As a result, the central surface path 1538 deviates from the first and second surface paths 1539 and 1537 in a direction towards the end upper section path 1526, thereby reducing the cross-section of the bridge 805 at the central surfaces 833 and 880. Moreover, in deviating towards the end upper section path 1526, the central surface path 1538 removes material from the bridge 805 to create the non-linear side portion 917 in the third surface 841 at the first side transition 836 and the non-linear side portion 918 in the fourth surface 842 at the first side transition 837. The non-linear shape of the end lower section path 1536 ensures the removal of material between a plane tangent to the central surface 880 and the first and second surfaces 881 and 882 such the bridge 805 presents a profile lower than bridges with a linear profile. At the first and second leg transitions 893 and 894, the machine transitions to the first corner set path 1524 and follows an inner corner path 1540 to cut an inner end portion of the corners 806 and 807. The machine transitions from the inner corner path 1540 to the leg path 1521 and follows an inner side leg path 1541 until the point 1520 to cut inner side portions of the legs 801 and 802.

The cutting machine begins at point 1620 and traces the path 1511. In particular, the machine follows an outer side leg path 1622 of a leg path 1621 and cuts an outer face portion of the legs 801 and 803. At the end of the outer side leg path 1622, the machine transitions to a first corner set path 1624 and follows an outer corner path 1625 to cut an outer side portion of the corners 806 and 808. The machine transitions from the outer corner path 1625 to a side upper section path 1626 at the first side transition 836. In the third embodiment, the side upper section path 1626 includes a third surface path 1627, a central surface path 1628, and a fourth surface path 1629. Following each of the third surface path 1627, the central surface path 1628, and the fourth surface path 1629 of the side upper section path 1626, the machine cuts the third surface 841, a portion of the central surface 833, and the fourth surface 843 of the first upper section 830 that lies between the side transitions 836 and 837. The side upper section path 1626 is non-linear in that it follows an arc between the side transitions 836 and 837. In particular, the third surface path 1627, the central surface path 1628, and the fourth surface path 1629 have a substantially similar arc radius in that the third surface path 1627, the central surface path 1628, and the fourth surface path 1629 follow a substantially uniform arc along the entire length of the side upper section path 1626, although the arc may flatten at the central surface 833 to provide a flattened profile of the bridge 805 at the central surface 833. The non-linear shape of the side upper section path 1626 ensures the removal of material between a plane tangent to the central surface 833 and the third and fourth surfaces 841 and 843 such the bridge 805 presents a profile lower than bridges with a linear profile. At the side transition 837, the machine transitions to a second corner set path 1630 and follows an outer corner path 1631 to cut an outer side portion of the corners 807 and 809. The machine transitions from the outer corner path 1631 to a leg path 1632 and follows an outer side leg path 1633 and an inner side leg path 1634 to cut outer and inner side portions of the legs 802 and 804. At the end of inner side leg path 1634, the machine transitions to the second corner set path 1630 and follows an inner corner path 1635 to cut an inner face portion of the corners 807 and 809. The machine transitions from the inner corner path 1635 to a side lower section path 1636 at the second side transition 889. In the third embodiment, the side lower section path 1636 includes a third surface path 1639, a central surface path 1638, and a fourth surface path 1637. Following the fourth surface path 1637, the central surface path 1638, and the third surface path 1639 of the side lower section path 1636, the machine cuts the fourth surface 884, a portion of the central surface 880, and the third surface 883 of the second lower section 831 that lies between the first and second side transitions 888 and 889. The side lower section path 1636 is non-linear in that it follows an arc between the first and second side transitions 888 and 889. In a first path configuration, the third surface path 1639, the central surface path 1638, and the fourth surface path 1637 have a substantially similar arc radius in that the third surface path 1639, the central surface path 1638, and the fourth surface path 1637 follow a substantially uniform arc along the entire length of the side lower section path 1636, although the arc may flatten at the central surface 880 to provide a flattened profile of the bridge 805 at the central surface 880. In an alternative path configuration according to the third embodiment, the third surface path 1639 and the fourth surface path 1637 have a substantially similar arc radius and follow a substantially symmetrical and uniform arc. The central surface path 1638, however, has an arc radius that is smaller than the arc radii of the third and fourth surface paths 1639 and 1637. As a result, the central surface path 1638 deviates from the third and fourth surface paths 1639 and 1637 in a direction towards the side upper section path 1626, thereby reducing the cross-section of the bridge 805 at the central surfaces 833 and 880. Moreover, in deviating towards the side upper section path 1626, the central surface path 1638 removes material from the bridge 805 to create the non-linear end portion 915 in the first surface 840 between the end transitions 871 and 875 and the non linear end portion 916 in the second surface 842 between the end transitions 872 and 876. The non-linear shape of the end lower section path 1636 ensures the removal of material between a plane tangent to the central surface 880 and the third and fourth surfaces 883 and 884 such the bridge 805 presents a profile lower than bridges with a linear profile. At the first side transition 888, the machine transitions to the first corner set path 1624 and follows an inner corner path 1640 to cut an inner side portion of the corners 806 and 808. The machine transitions from the inner corner path 1640 to the leg path 1621 and follows an inner side leg path 1641 until the point 1620 to cut inner side portions of the legs 801 and 803.

From the foregoing, it should be understood that producing the implant 810 from the billet 1500 using a method of manufacture wherein two intersecting non-linear paths are cut from two different directions results in the bridge 805 of implant 810 having a smooth reduced profile composite surface and a non-uniform cross-sectional area. In particular, cutting the non-linear end upper section path 1526 and the non-linear end lower section path 1536 from a first direction relative to the billet 1500 and cutting the non-linear side upper section path 1626 and the non-linear side lower section path 1636 from a second direction relative to the billet 1500 creates the implant 810 having a bridge 805 with tapered first, second, third, and fourth surfaces 840-843 and 881-884. Moreover, the bridge 805 includes a non-uniform cross-sectional area as illustrated in FIGS. 34-36 and 38-40 such that the implant 810 includes a low profile and provides less of protuberance to a patient as well as increased bending strength.

It is clear that the advanced implant designs of implants 210, 810, and 1000 offer advantages over prior art implants. The advantages include:

- Compression resulting from either the motion of the legs relative to the bridge, or the motion of the bridge alone, or a combination of both.
- A lower profile bridge with less protuberance for a surgery patient by having tapered and beveled surfaces on the upper surface of the bridge.
- Bridge surfaces that are not orthogonal to each other, such that all surfaces exposed above the bone and under the skin of the patient are non-orthogonal.
- A bridge that changes cross section between the two legs such that at any point the height of the bridge is shorter and wider than the width of the legs.
- A method of manufacturing the advanced design implants that uses two orthogonal paths to create the implant in its converging shape.

A method of manufacturing that causes two paths to intersect such that the intersection becomes the perimeter and profile of a shape memory implant in its converging position.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims.

The invention claimed is:

1. An orthopedic implant, comprising:
a bridge including first and second ends and first and second sides;
a first leg extending from the first end of the bridge;
a second leg extending from the second end of the bridge;
the bridge, comprising a first section and a second section, wherein the first section comprises:
a central surface,
a first surface that tapers from the central surface to a first end transition at the first end of the bridge,
a second surface that tapers from the central surface to a second end transition at the second end of the bridge, and
the tapers of the first and second surfaces provide the first section with a non-uniform cross-section, thereby flattening the profile of the orthopedic implant; and
the orthopedic implant comprising a shape memory material such that the orthopedic implant is movable between an insertion shape and an implanted shape.

2. The orthopedic implant according to claim 1, wherein the first section further comprises:
a third surface that tapers from the central surface to a first side transition at the first side of the bridge;
a fourth surface that tapers from the central surface to a second side transition at the second side of the bridge; and
the tapers of the third and fourth surfaces provide the first section with a non-uniform cross-section, thereby flattening the profile of the orthopedic implant.

3. The orthopedic implant according to claim 2, wherein each of the first, second, third, and fourth surfaces taper from the central surface following a non-linear profile.

4. The orthopedic implant according to claim 2, wherein the first, second, third, and fourth surfaces are non-orthogonal, thereby providing the bridge with a non-uniform cross-section that flattens the profile of the orthopedic implant.

5. The orthopedic implant according to claim 1, wherein:
the first section is an upper section and the second section is a lower section; and
the second section, comprises:
a central surface,
a first surface that tapers from the central surface to the first leg at the first end of the bridge,
a second surface that tapers from the central surface to a second leg at the second end of the bridge, and
the tapers of the first and second surfaces provide the second section with a non-uniform cross-section, thereby flattening the profile of the orthopedic implant.

6. The orthopedic implant according to claim 5, wherein each of the first and second surfaces of the second section taper from the central surface of the second section following a non-linear profile.

7. The orthopedic implant according to claim 1, wherein the first and second legs move during movement of the orthopedic implant between its insertion shape and its implanted shape.

8. The orthopedic implant according to claim 1, wherein the bridge moves during movement of the orthopedic implant between its insertion shape and its implanted shape.

9. The orthopedic implant according to claim 1, wherein the first and second legs and the bridge move during movement of the orthopedic implant between its insertion shape and its implanted shape.

10. The orthopedic implant according to claim 1, further comprising third and fourth legs extending from the second section.

11. An orthopedic implant, comprising:
a bridge including first, second, third, and fourth corners;
a first leg extending from the first corner of the bridge;
a second leg extending from the second corner of the bridge;
a third leg extending from the third corner of the bridge;
a fourth leg extending from the fourth corner of the bridge;
the bridge, comprising a first section and a second section, wherein the first section comprises:
a central surface,
a first surface that tapers from the central surface to a first end transition at the first corner of the bridge and a second end transition at the second corner of the bridge,
a second surface that tapers from the central surface to a third end transition at the third corner of the bridge and a fourth end transition at the fourth corner of the bridge, and
the tapers of the first and second surfaces provide the first section with a non-uniform cross-section, thereby flattening the profile of the orthopedic implant; and
the orthopedic implant comprising a shape memory material such that the orthopedic implant is movable between an insertion shape and an implanted shape.

12. The orthopedic implant according to claim 11, wherein the first section further comprises:
a third surface that tapers from the central surface to a first side transition at the first section;
a fourth surface that tapers from the central surface to a second side transition at the first section; and
the tapers of the third and fourth surfaces provide the first section with a non-uniform cross-section, thereby flattening the profile of the orthopedic implant.

13. The orthopedic implant according to claim 12, wherein each of the first, second, third, and fourth surfaces taper from the central surface following a non-linear profile.

14. The orthopedic implant according to claim 12, wherein the first, second, third, and fourth surfaces are non-orthogonal, thereby providing the bridge with a non-uniform cross-section that flattens the profile of the orthopedic implant.

15. The orthopedic implant according to claim 11, wherein the first surface includes a non-linear end portion between the first and second corners of the bridge.

16. The orthopedic implant according to claim 11, wherein the second surface includes a non-linear end portion between the third and fourth corners of the bridge.

17. The orthopedic implant according to claim 12, wherein the third surface includes a non-linear end portion at the first side transition.

18. The orthopedic implant according to claim 12, wherein the fourth surface includes a non-linear end portion at the second side transition.

19. The orthopedic implant according to claim 11, wherein:
   the first section is an upper section and the second section is a lower section; and
   the second section, comprises:
      a central surface,
      a first surface that tapers from the central surface to a first leg transition at the first corner of the bridge and a second leg transition at the second corner of the bridge,
      a second surface that tapers from the central surface to a third leg transition at the third corner of the bridge and a fourth leg transition at the fourth corner of the bridge, and
      the tapers of the first and second surfaces provide the second section with a non-uniform cross-section, thereby flattening the profile of the orthopedic implant.

20. The orthopedic implant according to claim 19, wherein the second section further comprises:
   a third surface that tapers from the central surface to a first side transition at the second section;
   a fourth surface that tapers from the central surface to a second side transition at the second section; and
   the tapers of the third and fourth surfaces provide the second section with a non-uniform cross-section, thereby flattening the profile of the orthopedic implant.

21. The orthopedic implant according to claim 20, wherein each of the first, second, third, and fourth surfaces of the second section taper from the central surface of the second section following a non-linear profile.

22. The orthopedic implant according to claim 19, wherein the first surface includes a non-linear end portion between the first and second corners of the bridge.

23. The orthopedic implant according to claim 19, wherein the second surface includes a non-linear end portion between the third and fourth corners of the bridge.

24. The orthopedic implant according to claim 20, wherein the third surface includes a non-linear end portion at the first side transition.

25. The orthopedic implant according to claim 20, wherein the fourth surface includes a non-linear end portion at the second side transition.

26. The orthopedic implant according to claim 11, wherein the first, second, third, and fourth legs move during movement of the orthopedic implant between its insertion shape and its implanted shape.

27. The orthopedic implant according to claim 11, wherein the bridge moves during movement of the orthopedic implant between its insertion shape and its implanted shape.

28. The orthopedic implant according to claim 11, wherein the first, second, third, and fourth legs and the bridge move during movement of the orthopedic implant between its insertion shape and its implanted shape.

* * * * *